(12) United States Patent
Terpetschnig et al.

(10) Patent No.: US 9,110,069 B2
(45) Date of Patent: *Aug. 18, 2015

(54) LUMINESCENT COMPOUNDS

(71) Applicant: SETA BioMedicals, LLC, Urbana, IL (US)

(72) Inventors: Ewald A. Terpetschnig, Urbana, IL (US); Leonid D. Patsenker, Kharkov (UA); Larysa Markova, Kharkov (UA); Iryna A. Fedyunyaeva, Kharkov (UA); Olga S. Kolosova, Kharkov (UA); Olena M. Obukhova, Kharkov (UA); Anatoliy Tatarets, Kharkov (UA)

(73) Assignee: SETA BioMedicals, LLC, Urbana, IL (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/047,878

(22) Filed: Oct. 7, 2013

(65) Prior Publication Data

US 2014/0086844 A1    Mar. 27, 2014

Related U.S. Application Data

(63) Continuation of application No. 13/144,890, filed as application No. PCT/US2010/021282 on Jan. 15, 2010, now Pat. No. 8,552,027.

(60) Provisional application No. 61/145,045, filed on Jan. 15, 2009.

(51) Int. Cl.
| | |
|---|---|
| A61K 31/44 | (2006.01) |
| G01N 33/58 | (2006.01) |
| C07F 9/572 | (2006.01) |
| C09B 23/01 | (2006.01) |
| C09B 23/06 | (2006.01) |
| C09B 23/08 | (2006.01) |
| A61K 49/00 | (2006.01) |
| C12Q 1/02 | (2006.01) |
| C12Q 1/68 | (2006.01) |

(52) U.S. Cl.
CPC .......... *G01N 33/582* (2013.01); *A61K 49/0032* (2013.01); *C07F 9/5728* (2013.01); *C09B 23/0033* (2013.01); *C09B 23/0066* (2013.01); *C09B 23/06* (2013.01); *C09B 23/083* (2013.01); *C09B 23/086* (2013.01); *C12Q 1/02* (2013.01); *C12Q 1/6818* (2013.01); *C12Q 1/6869* (2013.01)

(58) Field of Classification Search
None
See application file for complete search history.

(56) References Cited

U.S. PATENT DOCUMENTS

| | | |
|---|---|---|
| 2005/0202565 A1 | 9/2005 | Terpetschnig et al. |
| 2007/0042398 A1 | 2/2007 | Peng et al. |
| 2007/0172832 A1 | 7/2007 | Lukhtanov et al. |
| 2010/0143960 A1 | 6/2010 | Bazin |

FOREIGN PATENT DOCUMENTS

WO    WO 2008/125788 A1    10/2008

OTHER PUBLICATIONS

CAS RN 953793-12-9 (entered into STN on Nov. 15, 2007).*
CAS RN 953793-13-0 (entered into STN on Nov. 15, 2007).*
English-language abstract of PCT Patent Application Publication No. WO 2008/125788 A1, Oct. 23, 2008.

* cited by examiner

*Primary Examiner* — Craig Ricci
(74) *Attorney, Agent, or Firm* — DASCENZO Intellectual Property Law, P.C.

(57) ABSTRACT

Dyes and photoluminescent compounds based on polymethine dyes that contain at least one alkyl-phosphonate or substituted alkyl-phosphonate group, including the synthetic precursors, methods of synthesis, and applications thereof. Certain embodiments include heterocyclic ring systems and polymethine linkages selected such that the resulting polymethine dye is a cyanine dye, a merocyanine dye or a styryl dye.

19 Claims, 2 Drawing Sheets

LUMINESCENT COMPOUNDS

CROSS-REFERENCE TO RELATED APPLICATIONS

This application is a continuation of and claims priority to U.S. patent application Ser. No. 13/144,890, filed on Sep. 20, 2011 which is a national stage filing under 35 U.S.C. 371 of International Application No. PCT/US2010/021282, filed Jan. 15, 2010, which claims the benefit of U.S. Provisional Application No. 61/145,045, filed Jan. 15, 2009. The complete disclosures of the above-identified applications are incorporated herein by reference for all purposes.

CROSS-REFERENCES TO RELATED MATERIALS

This application incorporates by reference in their entirety for all purposes all patents, patent applications (published, pending, and/or abandoned), and other patent and nonpatent references cited anywhere in this application. The cross-referenced materials include but are not limited to the following publications: Richard P. Haugland, HANDBOOK OF FLUORESCENT PROBES AND RESEARCH CHEMICALS ($6^{th}$ ed. 1996); JOSEPH R. LAKOWICZ, PRINCIPLES OF FLUORESCENCE SPECTROSCOPY ($2^{nd}$ Ed. 1999); RICHARD J. LEWIS, SR., HAWLEY'S CONDENSED CHEMICAL DICTIONARY ($12^{th}$ ed. 1993).

TECHNICAL FIELD

The invention relates to compounds based on cyanines, among others. More particularly, the invention relates to compounds based on cyanines containing alkyl-phosphonate and substituted alkyl-phosphonate residues including biologically active phosphate esters that are useful as dyes and luminescent reporters for assays and cell-based applications.

BACKGROUND

Colorimetric and/or luminescent compounds may offer researchers the opportunity to use color and light to analyze samples, investigate reactions, and perform assays, either qualitatively or quantitatively. Generally, brighter, more photostable reporters may permit faster, more sensitive, and more selective methods to be utilized in such research.

While a colorimetric compound absorbs light, and may be detected by that absorbance, a luminescent compound, or luminophore, is a compound that emits light. A luminescence method, in turn, is a method that involves detecting light emitted by a luminophore, and using properties of that light to understand properties of the luminophore and its environment. Luminescence methods may be based on chemiluminescence and/or photoluminescence, among others, and may be used in spectroscopy, microscopy, immunoassays, and hybridization assays, among others.

Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including extinction coefficient, excitation and emission spectrum, Stokes' shift, luminescence lifetime, and quantum yield. An extinction coefficient is a wavelength-dependent measure of the absorbing power of a luminophore. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. The luminescence lifetime is the average time that a luminophore spends in the excited state prior to returning to the ground state and emission of a photon. A quantum yield is the ratio of the number of photons emitted to the number of photons absorbed by a luminophore.

Luminescence methods may be influenced by extinction coefficient, excitation and emission spectra, Stokes' shift, and quantum yield, among others, and may involve characterizing fluorescence intensity, fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Luminescence methods have several significant potential strengths. First, luminescence methods may be very sensitive, because modern detectors, such as photomultiplier tubes (PMTs) and charge-coupled devices (CCDs), can detect very low levels of light. Second, luminescence methods may be very selective, because the luminescence signal may come almost exclusively from the luminophore.

Despite these potential strengths, luminescence methods may suffer from a number of shortcomings, at least some of which relate to the luminophore. For example, the luminophore may have an extinction coefficient and/or quantum yield that is too low to permit detection of an adequate amount of light. The luminophore also may have a Stokes' shift that is too small to permit effective detection of emission light without significant detection of excitation light. The luminophore also may have an excitation spectrum that does not permit it to be excited by wavelength-limited light sources, such as common lasers and arc lamps. The luminophore also may be unstable, so that it is readily bleached and rendered nonluminescent. The luminescent compound may not be passively able to pass the plasma membrane in cells due to the presence of one or more ionic charges. The luminophore also may have an excitation and/or emission spectrum that overlaps with the well-known autoluminescence of biological and other samples; such autoluminescence is particularly significant at wavelengths below about 600 nm. The luminophore also may be expensive, especially if it is difficult to manufacture.

SUMMARY

The invention relates generally to dyes and photoluminescent compounds based on polymethine dyes that contain at least one alkyl-phosphonate or substituted alkyl-phosphonate group, including the synthetic precursors, methods of synthesis, and applications thereof.

ABBREVIATIONS

The following abbreviations, among others, may be used in this application:

| Abbreviation | Definition |
|---|---|
| BSA | bovine serum albumin |
| Bu | butyl |
| DCC | dicyclohexylcarbodiimide |
| DMF | dimethylformamide |
| D/P | dye-to-protein ratio |
| Et | ethyl |
| g | grams |
| h | hours |
| HSA | human serum albumin |
| IgG | Immunoglobulin G |
| L | liters |
| m | milli ($10^{-3}$) |
| M | molar |
| Me | methyl |
| mol | moles |
| M.P. | melting point |
| nm | nanometer ($10^{-9}$ meter) |
| NHS | N-hydroxysuccinimide |
| NIR | near infrared |
| PBS | phosphate-buffered saline |
| Prop | propyl |
| TMS | tetramethylsilane |
| TSTU | N,N,N',N'-tetramethyl(succinimido)uronium tetrafluoroborate |
| μ | micro ($10^{-6}$) |

DETAILED DESCRIPTION OF THE INVENTION

Figure 1:
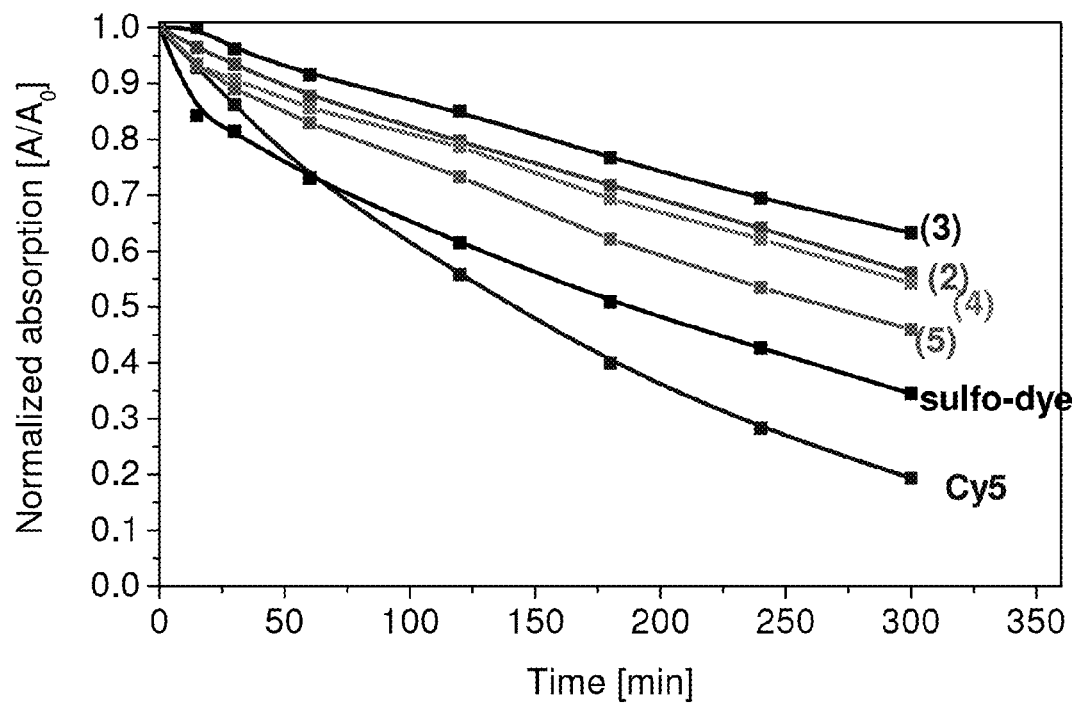
FIG. 1 is a plot showing the relative decrease in absorption upon exposure to light for selected dyes, as set forth in Example 15.

The invention relates generally to dyes and photoluminescent compounds containing at least one alkyl-phosphonate or substituted alkyl-phosphonate group including their synthetic precursors, and to methods of synthesizing and using such compounds. These compounds may be useful in both free and conjugated forms, as probes, labels, and/or indicators. This usefulness may reflect in part an enhancement of one or more of the following: quantum yield, Stokes' shift, extinction coefficients, aqueous solubility, photostability and chemical stability. Further specific derivatives of these esters can function as "biologically active" fluorescent compounds that may passively penetrate the plasma membranes of cells, where an intracellular conversion of the compounds into cell-impermeant forms result in the converted compounds remaining trapped within the cell membranes.

In one aspect, the invention relates to compositions that include reporter compounds that include or are substituted by at least one alkyl-phosphonate or substituted alkyl-phosphonate group.

These alkyl-phosphonate residues may either be neutral substituents that do not add additional formal charges to the overall molecule: —$(CH_2)_n$—$PO_3Et_2$ or —$(CH_2)_n$—$PO_3[(CH_2)_nCOOR]_2$, R=Me, Et or —$(CH_2)_n$—$PO_3[(CH_2)_nOH]_2$, —$(CH_2)_n$—$PO_3[CH_2O(C=O)CH_3]_2$, and/or they may include functionalities with reactive, —$(CH_2)_n$—$PO_3[(CH_2)_nCOONHS]_2$, ionic —$(CH_2)_n$—$PO_3[(CH_2)_nSO_3^-]_2$ and carrier groups —$(CH_2)_n$—$PO_3[(CH_2)_nCO—NH—S_c]_2$.

As shown in Example 15, the introduction of alkyl-phosphonate groups, such as —$(CH_2)_2$—$PO_3Et_2$, into cyanines may substantially increase their photostability up to twice as high as those of conventional cyanines, e.g. Cy5, a cyanine containing only sulfogroups.

This property may help produce dyes with higher photostability and excitation and emission in relatively inaccessible regions of the spectrum, including the red and near infrared.

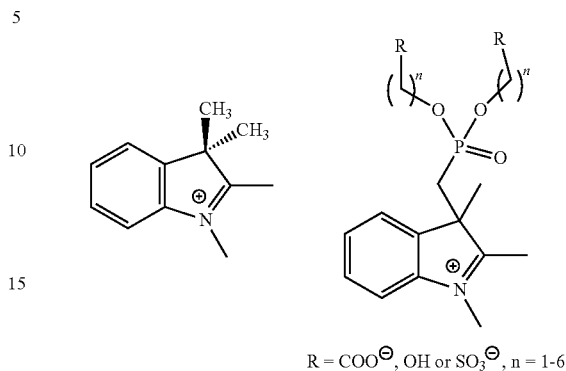

R = $COO^\ominus$, OH or $SO_3^\ominus$, n = 1-6

The alkyl-phosphonate [R—$(CH_2)_n$]— group in the structure above serves multiple purposes: either it may be used to help increase the photostability of a cyanine dye R=$CH_3$, n=1 (see above). Further the ethyl-phosphonate group can be easily used as a convenient starting functional group to introduce other residues (see Example 2), e.g. reactive groups (R=$(CH_2)_n$COOH, $(CH_2)_n$COO—NHS), ionic/hydrophilic groups (R=$(CH_2)_n$SO$_3^\ominus$, $(CH_2)_n$OH) or linked carriers (R=$(CH_2)_n$CO—NH—S$_c$).

As each phosphonate has 2 modifiable alkyl-substituents, the substitution with ionic groups such as e.g. sulfo-alkyl as described in 1t or 1u (Example 2), may provide a highly negatively charged functionality —$(CH_2)_n$—$PO_3[(CH_2)_nSO_3^-]_2$ that may improve the water-solubility of the final cyanine dye. Alternatively or in addition, the branched nature of these substituents (see Example 16, last structure and below) may also help in reducing the tendency of the compounds to form aggregates.

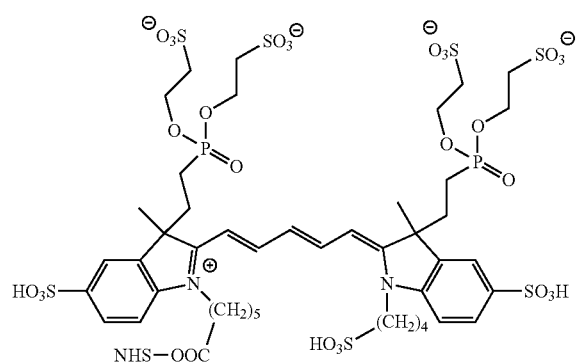

Ethyl-phosphonates can also be converted to "biologically active groups", which as outlined in an article by C. Schultz in Bioorganic & Medicinal Chemistry 11, 885-898, (2003) open up ways to produce non-charged compounds that are able to passively diffuse across the plasma membrane. Once inside the cells, the masking group, e.g. an aceteoxymethylene group, $(CH_2)_n$—$PO_3[CH_2O(C=O)CH_3]_2$ is removed by chemical or enzymatic hydrolysis, generating the charged phosphate or phosphonate ester, and thereby making the dye-molecule again impermeant to cell membranes and thereby preventing dye leakage from the cell.

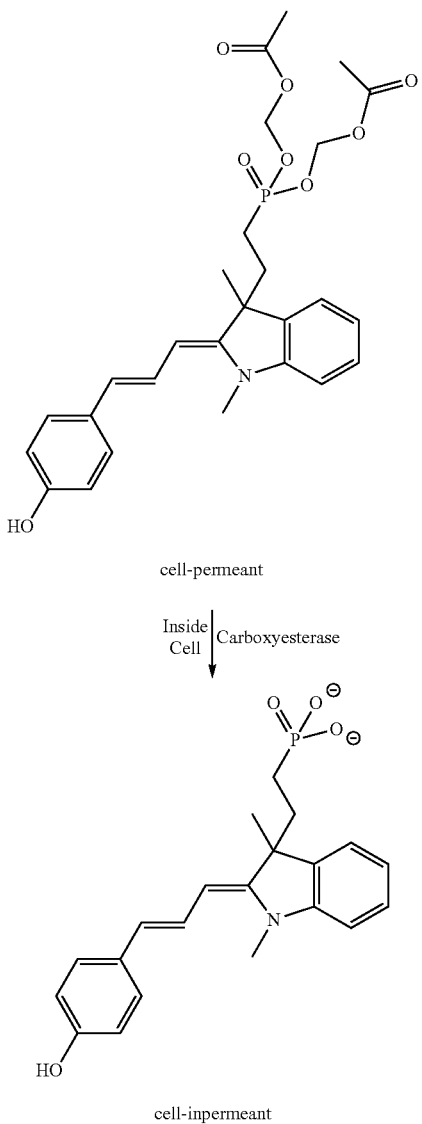

cell-permeant

Inside Cell | Carboxyesterase cell-inpermeant

The synthesis of these phosphate esters is described by D. N. Srivastva and D. Farquhar, Bioorg. Chem. 1984, 12, 118 and typically proceeds via an acyloxyalkyl halogenide, in the presence of a sterically hindered base, in a dry organic solvent.

The remaining discussion includes (1) an overview of structures, (2) an overview of synthetic methods, and (3) a discussion of the applications of the invention.

Overview of Structures

The reporter compounds are typically polymethine dyes, such as cyanine dyes, merocyanine dyes, and styryl dyes. These dyes are characterized in that they typically include at least one of the following heterocyclic moieties:

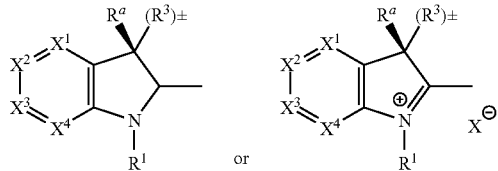

where $X^-$ represents an anion;

$R^1$ is selected from H, L-$S_c$, L-Rx, L-$R^x$, —$CH_2$—CONH—$SO_2$-Me, L-$PO_3^{2\ominus}$, L-O—$PO_3^{2\ominus}$, L-$PO_3R^{m\ominus}$, L-O—$PO_3R^{m\ominus}$, aliphatic groups, alicyclic groups, alkylaryl groups, aromatic groups, each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium; and L is a single covalent bond or is a covalent linkage that is linear or branched, cyclic or heterocyclic, saturated or unsaturated, having 1-20 nonhydrogen atoms from the group of C, N, P, O and S, in such a way that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^x$ is a reactive group;

$S_c$ is a conjugated substance;

$R^\pm$ is an ionic group;

$R^a$ may be, H, L-$S_c$, L-$R^x$, L-$R^\pm$, —$CH_2$—CONH—$SO_2$-Me, aliphatic, alicyclic, aromatic, alkyl-aryl, F, Cl, Br, I, $NH_2$, —COOH, —CN, azido, —OH, —$NO_2$, —$SO_3H$, —$SO_2NHR^m$, —$SO_2NHNH$—$R^m$, —$SO_2R^f$, —$C_6H_4$—$SO_3^\ominus$, —$C_6H_4$—$PO_3^\ominus$, pyridylium, pyrylium, —$PO_3^{2\ominus}$, —O—$PO_3^{2\ominus}$, —$PO_3R^{m\ominus}$, —O—$PO_3R^{m\ominus}$, —$CONH_2$, $CONHR^m$, —$CONHNHR^m$, COO—NHS and COO—$R^m$;

$(R^3)^\pm$ is selected from L-$PO_3R^{m\ominus}$, L-$PO_3R^m_2$;

$R^m$ is selected from a group consisting of L-$S_c$, L-$R^x$, L-$R^\pm$, aliphatic substituents, aromatic substituents; each aliphatic residue may incorporate up to six heteroatoms selected from N, O, S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

$R^f$ is selected from alkyl, —$CH_2F$, $CHF_2$, $CF_3$;

each of $X^1$, $X^2$, $X^3$, and $X^4$ are independently selected from the group consisting of N, $NR^t$, O, S, and C—$R^t$, wherein $R^t$ is hydrogen, L-$S_c$, L-$R^x$, L-$R^\pm$, —$CH_2$—CONH—$SO_2$-Me, L-$PO_3R^{n\ominus}$, L-$PO_3R_2^n$, or an aliphatic, alicyclic, or aromatic group; amino, sulfo, trifluoromethyl, alkoxy, halogen, carboxy, hydroxy, phosphate, phosphonate, sulfate; or adjacent $R^t$ substituents, taken in combination, form a fused aromatic or heterocyclic ring that is itself optionally further substituted by H, L-$S_c$, L-$R^x$, L-$R^\pm$, alkyl, aryl or cycloalkyl.

$R^n$ is selected from a group consisting of L-$S_c$, L-$R^x$, L-$R^\pm$.

The substituents on the substituted rings may be chosen quite broadly, and may include the various component listed above, among others.

In one aspect of the invention, the reporter compounds are described by the following structure:

Here, Z is a single carbon-center, a partially-conjugated four- five- or six-member ring-system, and A, B, and C are substituents of Z; Z is a single carbon-center or part of a partially-conjugated four- five or six-member ring system, and A is represented by $R^\tau$ and B or C is one of $W^1$ and $W^2$

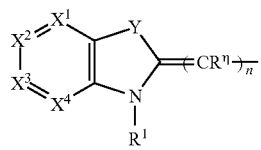

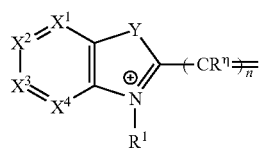

The components $R^1$, $R^\eta$, $R^\tau$, n, m, $X^1$, $X^2$, $X^3$, $X^4$, and Y are defined in detail in the Detailed Description. However, generally, each compound includes at least one of $W^1$ or $W^2$ with the preferred synthetic precursors including one, and the preferred reporter compounds including two. Alternatively, or in addition, the compound may include at least one heteroatom in $X^1$ through $X^4$ of $W^1$, $W^2$ or $W^3$. Alternatively, or in addition, the compound may include a reactive group and/or a carrier.

Reporter Compounds

The reporter compounds may be colorimetric dyes, useful as stains and for colorimetric detection. Alternatively or in addition, the reporter compounds may be photoluminescent, particularly fluorescent, and may have utility in photoluminescence assays and methods, as discussed above. All compounds are characterized that they contain at least one phosphonate or substituted phosphonate group in the heterocyclic base.

Tandems

Reporter compounds in accordance with the invention also may include pairs, triplets, and higher numbers of compounds conjugated together to form a single compound. Such "tandems" may be used to obtain alternative spectral properties, such as enhanced Stokes' shifts. Such tandems may be based on the principle of energy transfer. Some potential combinations are drawn below, where B and C, $W^1$, $W^2$ and Z have their usual meanings, and U represents a cross-link, such as may be formed by cross-reaction using a reactive compound. U can be also be chosen so that the two pairs become a larger conjugated system linked via a C—C-triple-bond as described by K. Burgess, Chem. Eur. J. 2003, 9, 4430-4441. Z and each substituent may be chosen independently for each component of a tandem.

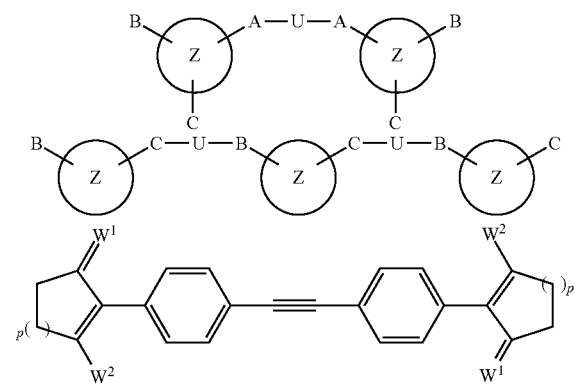

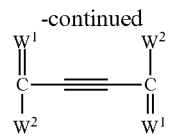

Reactive Groups $R^x$

The substituents of Z may include one or more reactive groups, where a reactive group generally is a group capable of forming a covalent attachment with another molecule or substrate. Such other molecules or substrates may include proteins, carbohydrates, nucleic acids, and plastics, among others. Reactive groups vary in their specificity, and may preferentially react with particular functionalities and molecule types. Thus, reactive compounds generally include reactive groups chosen preferentially to react with functionalities found on the molecule or substrate with which the reactive compound is intended to react.

The compounds of the invention are optionally substituted, either directly or via a substituent, by one or more chemically reactive functional groups that may be useful for covalently attaching the compound to a desired substance. Each reactive group, or $R^x$, may be bound to the compound directly by a single covalent bond, or may be attached via a covalent spacer or linkage, L, and may be depicted as -L-$R^x$.

The reactive functional group of the invention $R^x$ may be selected from the following functionalities, among others: activated carboxylic esters, acyl azides, acyl halides, acyl halides, acyl nitriles, acyl nitriles, aldehydes, ketones, alkyl halides, alkyl sulfonates, anhydrides, aryl halides, aziridines, boronates, carboxylic acids, carbodiimides, diazoalkanes, epoxides, haloacetamides, halotriazines, imido esters, isocyanates, isothiocyanates, maleimides, phosphoramidites, silyl halides, sulfonate esters, and sulfonyl halides.

In particular, the following reactive functional groups, among others, are particularly useful for the preparation of labeled molecules or substances, and are therefore suitable reactive functional groups for the purposes of the reporter compounds:

a) N-hydroxysuccinimide esters, isothiocyanates, and sulfonylchlorides, which form stable covalent bonds with amines, including amines in proteins and amine-modified nucleic acids;

b) Iodoacetamides and maleimides, which form covalent bonds with thiol-functions, as in proteins;

c) Carboxyl functions and various derivatives, including N-hydroxybenztriazole esters, thioesters, p-nitrophenyl esters, alkyl, alkenyl, alkynyl, and aromatic esters, and acyl imidazoles;

d) Alkylhalides, including iodoacetamides and chloroacetamides;

e) Hydroxyl groups, which can be converted into esters, ethers, and aldehydes;

f) Aldehydes and ketones and various derivatives, including hydrazones, oximes, and semicarbozones;

g) Isocyanates, which may react with amines;

h) Activated C=C double-bond-containing groups, which may react in a Diels-Alder reaction to form stable ring systems under mild conditions;

i) Thiol groups, which may form disulfide bonds and react with alkylhalides (such as iodoacetamide);

j) Alkenes, which can undergo a Michael addition with thiols, e.g., maleimide reactions with thiols;

k) Phosphoramidites, which can be used for direct labeling of nucleosides, nucleotides, and oligonucleotides, including primers on solid or semi-solid supports;

l) Primary amines that may be coupled to variety of groups including carboxyl, aldehydes, ketones, and acid chlorides, among others;
m) Boronic acid derivatives that may react with sugars
n) Pyrylium moieties react with primary amines.
o) Haloplatinates form stable platinum complexes with amines, thiols and heterocycles
p) Aryl halides react with thiols and amines R Groups The R moieties associated with the various substituents of Z may include any of a number of groups, as described above, including but not limited to alicyclic groups, aliphatic groups, aromatic groups, and heterocyclic rings, as well as substituted versions thereof.

Aliphatic groups may include groups of organic compounds characterized by straight- or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked and may contain one or more heteroatoms (such as polyethers and polyamines, among others).

As used herein, "alicyclic groups" include hydrocarbon substituents that incorporate closed rings. Alicyclic substituents may include rings in boat conformations, chair conformations, or resemble bird cages. Most alicyclic groups are derived from petroleum or coal tar, and many can be synthesized by various methods. Alicyclic groups may optionally include heteroalicyclic groups that include one or more heteroatoms, typically nitrogen, oxygen, or sulfur. These compounds have properties resembling those of aliphatics and should not be confused with aromatic compounds having the hexagonal benzene ring. Alicyclics may comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aromatic groups may include groups of unsaturated cyclic hydrocarbons containing one or more rings. A typical aromatic group is benzene, which has a 6-carbon ring formally containing three double bonds in a delocalized ring system. Aromatic groups may be highly reactive and chemically versatile. Most aromatics are derived from petroleum and coal tar. Heterocyclic rings include closed-ring structures, usually of either 5 or 6 members, in which one or more of the atoms in the ring is an element other than carbon, e.g., sulfur, nitrogen, etc. Examples include pyridine, pyrole, furan, thiophene, and purine. Some 5-membered heterocyclic compounds exhibit aromaticity, such as furans and thiophenes, among others, and are analogous to aromatic compounds in reactivity and properties.

Any substituent of the compounds of the invention, including any aliphatic, alicyclic, or aromatic group, may be further substituted one or more times by any of a variety of substituents, including without limitation, F, Cl, Br, I, carboxylic acid, sulfonic acid, CN, nitro, hydroxy, phosphate, phosphonate, sulfate, cyano, azido, amine, alkyl, alkoxy, trialkylammonium or aryl. Aliphatic residues can incorporate up to six heteroatoms selected from N, O, S. Alkyl substituents include hydrocarbon chains having 1-22 carbons, more typically having 1-6 carbons, sometimes called "lower alkyl".

As described in WO01/11370, sulfonamide groups such as —$(CH_2)_n$—$SO_2$—NH—$SO_2$—R, —$(CH_2)_n$—CONH—$SO_2$—R, —$(CH_2)_n$—$SO_2$—NH—CO—R, and —$(CH_2)_n$—$SO_2$NH—$SO_3$H, where R is aryl or alkyl and n=1-6, can be used to reduce the aggregation tendency and have positive effects on the photophysical properties of cyanines and related dyes, in particular when these functionalities are directly associated with the benzazole ring in position 1 (the nitrogen atom in the azole ring).

Where a substituent R is further substituted by a functional group that is formally electronically charged, such as for example a carboxylic acid, sulfonic acid, phosphoric acid, phosphonate or a quaternary ammonium group, the resulting ionic substituent $R^\pm$ may serve to increase the overall hydrophilicity of the compound. Examples of electronically charged functional groups include —$PO_3^{2\ominus}$, —O—$PO_3^{2\ominus}$, —$PO_3R^{m\ominus}$, —O—$PO_3R^{m\ominus}$, —$C_6H_4$—$SO_3^\ominus$, —$C_6H_4$—$PO_3^\ominus$, pyridylium, pyrylium, —$SO_3^\ominus$, —O—$SO_3^\ominus$, —$COO^\ominus$ and ammonium, among others.

As used herein, functional groups such as "carboxylic acid," "sulfonic acid," and "phosphoric acid" include the free acid moiety as well as the corresponding metal salts of the acid moiety, and any of a variety of esters or amides of the acid moiety, including without limitation alkyl esters, aryl esters, and esters that are cleavable by intracellular esterase enzymes, such as alpha-acyloxyalkyl ester (for example acetoxymethylene esters, among others). Further these esters might contain additional reactive or ionic groups and linked carriers.

The compounds of the invention are optionally further substituted by a reactive functional group $R^x$, or a conjugated substance $S_c$, as described below.

The compounds of the invention may be depicted in structural descriptions as possessing an overall charge, it is to be understood that the compounds depicted include an appropriate counter ion or counter ions to balance the formal charge present on the compound. Further, the exchange of counter ions is well known in the art and readily accomplished by a variety of methods, including ion-exchange chromatography and selective precipitation, among others.

Carriers and Conjugated Substances $S_c$

The reporter compounds of the invention, including synthetic precursor compounds, may be covalently or non-covalently associated with one or more substances. Covalent association may occur through various mechanisms, including a reactive functional group as described above, and may involve a covalent linkage, L, separating the compound or precursor from the associated substance (which may therefore be referred to as -L-$S_c$).

The covalent linkage L binds the reactive group $R^x$, the conjugated substance $S_c$ or the ionic group $R^\pm$ to the dye molecule, either directly (L is a single bond) or with a combination of stable chemical bonds, that include single, double, triple or aromatic carbon-carbon bonds; carbon-sulfur bonds, carbon-nitrogen bonds, phosphorus-sulfur bonds, nitrogen-nitrogen bonds, nitrogen-oxygen or nitrogen-platinum bonds, or aromatic or heteroaromatic bonds; L includes ether, thioether, carboxamide, sulfonamide, urea, urethane or hydrazine moieties. Preferable L include a combination of single carbon-carbon bonds and carboxamide or thioether bonds.

Where the substance is associated noncovalently, the association may occur through various mechanisms, including incorporation of the compound or precursor into or onto a solid or semisolid matrix, such as a bead or a surface, or by nonspecific interactions, such as hydrogen bonding, ionic bonding, or hydrophobic interactions (such as Van der Waals forces). The associated carrier may be selected from the group consisting of polypeptides, polynucleotides, polysaccharides, beads, microplate well surfaces, metal surfaces, semiconductor and non-conducting surfaces, nano-particles, and other solid surfaces.

The associated or conjugated substance may be associated with or conjugated to more than one reporter compound, which may be the same or different. Generally, methods for the preparation of dye-conjugates of biological substances are well-known in the art. See, for example, Haugland et al., MOLECULAR PROBES HANDBOOK OF FLUORESCENT PROBES AND RESEARCH CHEMICALS, Eighth Edition (1996), which is hereby incorporated by reference. Typically, the association or conjugation of a chromophore or luminophore to a substance imparts the spectral properties of the chromophore or luminophore to that substance.

Useful substances for preparing conjugates according to the present invention include, but are not limited to, amino acids, peptides, proteins, nucleosides, nucleotides, nucleic acids, carbohydrates, lipids, ion-chelators, nonbiological polymers, cells, and cellular components. The substance to be conjugated may be protected on one or more functional groups in order to facilitate the conjugation, or to insure subsequent reactivity.

Where the substance is a peptide, the peptide may be a dipeptide or larger, and typically includes 5 to 36 amino acids. Where the conjugated substance is a protein, it may be an enzyme, an antibody, lectin, protein A, protein G, hormones, or a phycobiliprotein. The conjugated substance may be a nucleic acid polymer, such as for example DNA oligonucleotides, RNA oligonucleotides (or hybrids thereof), or single-stranded, double-stranded, triple-stranded, or quadruple-stranded DNA, or single-stranded or double-stranded RNA.

Another class of carriers includes carbohydrates that are polysaccharides, such as dextran, heparin, glycogen, starch and cellulose.

Where the substance is an ion chelator, the resulting conjugate may be useful as an ion indicator (calcium, sodium, magnesium, zinc, potassium and other important metal ions) particularly where the optical properties of the reporter-conjugate are altered by binding a target ion. Preferred ion-complexing moieties are crown ethers (U.S. Pat. No. 5,405,957) and BAPTA chelators (U.S. Pat. No. 5,453,517).

The associated or conjugated substance may be a member of a specific binding pair, and therefore useful as a probe for the complementary member of that specific binding pair, each specific binding pair member having an area on the surface or in a cavity which specifically binds to and is complementary with a particular spatial and polar organization of the other. The conjugate of a specific binding pair member may be useful for detecting and optionally quantifying the presence of the complementary specific binding pair member in a sample, by methods that are well known in the art.

Representative specific binding pairs may include ligands and receptors, and may include but are not limited to the following pairs: antigen-antibody, biotin-avidin, biotin-streptavidin, IgG-protein A, IgG-protein G, carbohydrate-lectin, enzyme-enzyme substrate; ion-ion-chelator, hormone-hormone receptor, protein-protein receptor, drug-drug receptor, DNA-antisense DNA, and RNA-antisense RNA.

Preferably, the associated or conjugated substance includes proteins, carbohydrates, nucleic acids, and nonbiological polymers such as plastics, metallic nanoparticles such as gold, silver and carbon nanostructures among others. Further carrier systems include cellular systems (animal cells, plant cells, bacteria). Reactive dyes can be used to label groups at the cell surface, in cell membranes, organelles, or the cytoplasm.

Finally these compounds can be linked to small molecules such as amino acids, vitamines, drugs, haptens, toxins, environmental pollutants. Another important ligand is tyramine, where the conjugate is useful as a substrate for horseradish peroxidase. Additional embodiments are described in U.S. Patent Application Publication No. US 2002/0077487.

Synthesis

The synthesis of the disclosed reporter compounds typically is achieved in a multi-step reaction, starting with the synthesis of a methylene base. The synthesis of suitable methylene bases may proceed based on literature or novel methods. Generally, the spectral properties of the reporter compounds, including excitation and emission wavelengths for luminescent compounds, may be strongly dependent on the type of methylene base used. Typical starting materials include quarternized indolenines, benzthiazoles, benzoxazoles, benzimidazoles, etc., N,N'-diphenylformamidine, and malonaldehyde bis(phenylimine) monohydrochloride, among others.

The majority of current indolenine-cyanine labels are either based on indolenines that are exclusively 3,3'-dimethyl indolenines (Mujumdar et al., Bioconjugate Chem. 4(2) 105-111, 1993; U.S. Pat. No. 4,981,977, Southwick et al.; U.S. Pat. No. 5,268,486 Waggoner et al.; U.S. Pat. No. 5,486,616 Waggoner et al.) or 3-methyl-3'-alkyl indolenines wherein the alkyl linker is either modified to contain a reactive $C_6$-linker (U.S. Pat. No. 6,258,340; Licha et al. and U.S. Pat. No. 6,977,305; Leung et al.) or a sulfo-group with a $C_3$ or $C_4$-linker (U.S. Pat. No. 6,258,340; Licha et al. and US patent application 2007/0128659A1; Czerney et al). Compounds with shorter linkers to these sulfo-groups are claimed but have not been reduced to practice.

One of the preferred ways of synthesis of these novel methylene-bases is via a "Fischer-Indole Synthesis" using substituted phenyl-hydrazines and substituted aliphatic ketones:

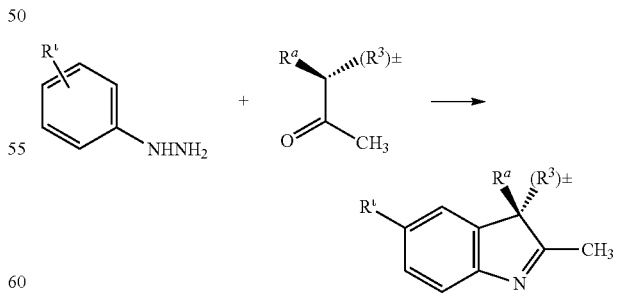

Starting materials like ethyl 2-methylacetoacetate are also readily available from Aldrich. The reaction of this starting material with 4-hydrazinobenzenesulfonic acid according to the procedure of K. Liu et al., Org. Lett., 2006, 8 (25), 5769-5771 is described below.

The new indolenine intermediates, synthesized via the "Fischer-Indole synthesis" (see above) are subsequently quarternized with alkylating agents such as methyl iodide, propanesultone, butanesultone or bromo-hexanoic acid. The synthesis of other key-compounds for these novel cyanines are described in Examples 1 and 2, while the methods for the synthesis of representative dyes of this invention are provided in Examples 3-12.

The dye molecules of this invention typically consist of a bridging unit and the heterocyclic bases $W^1$ and $W^2$. The bridging unit is either a simple polymethine chain of various lengths or it can be substituted by a cyclo-alkene. When the bridging unit is a polymethine chain the coupling agent can be N,N-diphenylformamidine, triethylorthoformate, or malonaldehyde bis(phenylimine) hydrochloride, 1,1,3-trimethoxypropane, 1,1,3,3-tetramethoxypropane and glutaconaldehyde dianil monohydrochloride.

The synthesis of various classes of polymethine dyes is very well described in the book by Gupta RR, Strekowski L (eds) (2008) Heterocyclic polymethine dyes. Topics in Heterocyclic Chemistry, vol. 14. Springer-Verlag, Berlin, Heidelberg. Other resources are A. Mishra et al., Cyanines during the 1990s: a review. Chem. Rev. 100, 1973-2011 (2000), and Gonçalves et al., Fluorescent labeling of biomolecules with organic probes. Chem. Rev. 109, 190-212, (2009).

To further enhance water-solubility, sulfonic acid or other groups including quaternary ammonium, polyether, carboxyl, and phosphate, among others, may be introduced into the heterocyclic ring systems or in the bridging unit. In order to facilitate covalent attachment to proteins, reactive N-hydroxy-succinimide ester (NHS ester) or other reactive derivatives may be synthesized.

The synthesis of cyanine dyes is described in Mujumdar et al., Bioconjugate Chem. 4(2) 105-111, 1993 and in several other patent applications (U.S. Patent Appl. US 2002/0077487 A1, U.S. patent application US2003/0170179, U.S. Pat. No. 5,569,587, U.S. Pat. No. 5,672,027, U.S. Pat. No. 5,808,044, U.S. patent application US2006/0280688, U.S. patent application US2004/0014981, and WO 2004/039894, which are incorporated herein as reference).

The cyanine dyes of this invention exhibit absorption maxima in the range between 500 and 850 nm. In addition to a variety of other structural parameters, the selection of a monomethine, trimethine, or pentamethine linkages permits the spectral properties of the resulting compound to be altered according to the characteristics desired. For example, where the remainder of the compound is held constant, shifting from a monomethine to a trimethine, pentamethine or heptamethine linkage in a $W^1$ or $W^2$ substituent typically results in a shifting of the absorption and emission wavelengths of the resulting compounds to progressively longer wavelengths. The absorption maxima can be fine-tuned by additional introduction of functional groups to match the emission lines of a frequency-doubled Nd-Yag laser (532 nm), Kr-ion laser (568 and 647 nm), the HeNe laser (543 nm and 633 nm) and diode lasers (635 nm, 650 nm, 780 nm etc.). Cyanine dyes exhibit a lesser tendency to change their quantum yields upon changing the environment (e.g. labelling to a protein).

Many compounds of the invention possess an overall electronic charge. It is to be understood that when such electronic charges are present, that they are balanced by an appropriate counterion, which may or may not be identified.

EXAMPLE 1

Synthesis of Precursors and Intermediates

This section describes the synthesis of various precursors and intermediates for the synthesis of novel cyanine dyes. p-hydrazinobenzenesulfonic acid (Illy et al., J. Org. Chem. 33, 4283-4285 1968), 2,3,3-trimethylindole-5-sulfonic acid potassium salt (1a), 1-(5-carboxypentyl)-2,3,3-trimethyl-3H-5-indoliumsulfonate (1b), 1-(4-sulfonatobutyl)-2,3,3-trimethylindoleninium-5-sulfonate (1h) (Mujumdar et al., Bioconjugate Chem. 4(2) 105-111, 1993), and 1,2,3,3-tetramethylindoleninium-5-sulfonate (1c) were synthesized using literature procedures. 1d-1f are synthesized according to the procedures provided in U.S. Patent Application Publication No. US 2002/0077487. 1-(2-phosphonethyl)-2,3,3-trimethylindoleninium-5-sulfonate is described in PCT Patent Application Publication No. WO 01/36973.

The synthesis of sulfonated benzindolenines and other cyclo-condensed heterocycles is described in U.S. Patent Application Publication No. US 2002/0077487 and U.S. Pat. No. 6,140,494 and by S. Mujumdar et al. Bioconjugate Chem. 1996, 7, 356-362.

It is also understood that the additional aromatic ring can be fused at different positions onto the parent heterocycle (see WO02/26891 A1) and Mujumdar et al. Bioconjugate Chem. 1996, 7, 356-362.

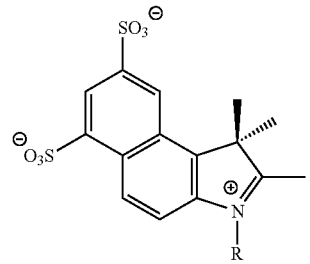

The synthesis of heterocyclic compounds containing additional heteroatoms is also described in U.S. Patent Application Publication No. US 2002/0077487.

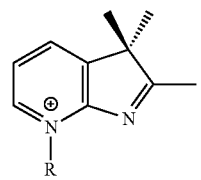

Synthesis of p-hydrazinobenzenesulfonic acid 33 g of sodium carbonate was added to a suspension of 104 g (0.6 mol) of p-aminobenzenesulfonic acid in 400 mL of hot water. The solution was cooled to 5° C. in an ice-bath, and 70 g of concentrated sulfuric acid were added slowly under rapid stirring. A solution of 42 g of sodium nitrite in 100 mL of water was then added under cooling. A light yellow diazo-compound precipitate formed, which was filtered and washed with water, but not dried.

The wet diazo-compound was added under stirring and cooling (5° C.) to a solution of 170 g of sodium sulfite in 500 mL of water. The solution, which turned orange, was stirred under cooling for 1 h, and then heated to reflux. Finally, 400 mL of concentrated hydrochloric acid were added. The solution turned yellow, and the product precipitated as a white solid. For complete decoloration, 1-2 g of powdered zinc were added. The reaction mixture was cooled overnight, and the precipitate was filtered, washed with water, and dried in an oven at 100° C.

Yield: 96 g (85%), white powder; M.P.=286° C. (Lit.=285° C.); $R_f$: 0.95 (RP-18, water:MeOH 2:1).

Synthesis of 2,3,3-trimethylindole-5-sulfonic acid, potassium salt (1a)

18.2 g (0.12 mol) of p-hydrazinobenzenesulfonic acid and 14.8 g (0.17 mol) of isopropylmethylketone were stirred in 100 mL of glacial acetic acid at room temperature for 1 h. The mixture was then refluxed for 4 h. The mixture was cooled to room temperature, and the resulting pink solid precipitate was filtered and washed with ether.

The precipitate was dissolved in methanol, and a concentrated solution of potassium hydroxide in 2-propanol was added until a yellow solid completely precipitated. The precipitate was filtered, washed with ether, and dried in a desiccator over $P_2O_5$.

Yield: 20.4 g (71%), off-white powder; M.P.=275° C.; $R_f$: 0.40 (silica gel, isopropanol:water:ammonia 9:0.5:1).

1-(5-carboxypentyl)-2,3,3-trimethyl-3H-5-indolium-sulfonate (1b)

15.9 g (57 mmol) of 2,3,3-trimethylindolenium-5-sulfonic acid potassium salt 1a and 12.9 g (66 mmol) of 6-bromohexanoic acid were refluxed in 100 mL of 1,2-dichlorobenzene for 15 min under a nitrogen atmosphere. The solution was cooled to room temperature, and the resulting pink precipitate was filtered, washed with chloroform, and dried.

Yield: 15.8 g (58%), pink powder; $R_f$: 0.75 (RP-18, MeOH: water 2:1).

Synthesis of 1,2,3,3-tetramethylindolium-5-sulfonate (1c)

1.1 g of 2,3,3-trimethylindoleninium-5-sulfonate were suspended in 30 mL of methyl iodide. The reaction mixture was heated to boiling for h in a sealed tube. After the mixture was cooled, excess methyl iodide was decanted, and the residue was suspended in 50 mL of acetone. The solution was filtered, and the residue was dried in a desiccator over $CaCl_2$. The resulting light yellow powder was used without further purification.

Yield: 90%, light yellow powder.

Synthesis of 3-(5-carboxypentyl)-2,3-dimethyl-5-sulfo-1-(3-sulfopropyl) indolium sodium salt (1d), (Scheme I)

A mixture of 25 g of ethyl 2-methylacetoacetate (I), 64 ml of 21% sodium ethoxide solution in ethanol and 34 mL of ethyl-6-bromohexanoate is refluxed in 200 mL of ethanol overnight. The mixture is filtered and the solvent is removed under reduced pressure. The residue is partitioned between 1 M HCl and chloroform.

The organic layer is dried over magnesium sulfate and purified on silica gel using 1:10 ethyl acetate/hexane as the eluent to yield 22 g of ethyl 2-(5-carboethoxypentyl)-2-methylactoacetate (IIa)

The above compound is dissolved in 300 ml of methanol. A solution of 10 g NaOH in 100 mL water is added. The mixture is heated at 50° C. overnight. The solution is reduced to about 50 mL, acidified to pH 1 and extracted with ethyl acetate. The organic phase is collected, dried over $MgSO_4$ and evaporated to yield 13.5 g of 7-methyl-8-oxononanoic acid (IIIa).

The nonanonic acid is refluxed in 110 mL of acetic acid with 13.5 g of 4-hydrazinobenzenesulfonic acid for 4 hours. The acetic acid is evaporated and the product is purified on silica gel to yield 23 g of the product (IVa).

To the methanol solution of 11 g of Compound IVa is added 3.4 g of anhydrous sodium acetate. The mixture is stirred for five minutes. The solvent is evaporated and the resulting sodium salt is heated with 24.4 g of propane sultone at 110° C. for 1 hour to generate the final product 1d.

Synthesis of 3-(6-hydroxyhexyl)-2,3-dimethyl-5-sulfo-1-(3-sulfopropyl) indolium, sodium salt (1e)

Another starting material 1e is synthesized analogously using ethyl 2-methylacetoacetate and 6-benzoyl-1-bromo-hexane in the presence of 1.2 equivalents of sodium hydride in THF according to 1d. After isolating the 3-(6-hydroxy-hexyl)-2,3-dimethyl-5-sulfo-indolium, inner salt (the hydroxy group is again protected and the compound is quarternized using propanesultone. Deprotection is achieved using dilute NaOH.

1f is synthesized analogously taking into account the more polar nature of the sulfonic groups that are introduced either by reaction with 2-bromo-ethane-sulfonic acid, propane- or butanesultone. Sulfogroups can also be introduced by reaction of a 3-carboxy-alkyl-substituted compound like 1d with taurine according to Terpetschnig et al. Anal. Biochem. 217, 197-204 (1994).

Using 4-hydrazino-benzoic acid as described in Anal. Biochem. 217, 197-204 (1994) or 4-hydrazino-phenyl-acetic acid as described in Cytometry 11(3), 418-30 (1990) and reacting them in a Fischer indole synthesis with 7-methyl-8-oxononanoic acid or one of the other functionalized precursors as described above, 5-carboxy-derivatized indoles such as 1 g that contain a spacer group in position 3 can be synthesized.

Other compounds that contain functional groups in both $R^3$ and $R^4$ can be synthesized as described below and used as starting materials for cyanine dyes of this invention. $R^3$ and $R^4$ can also be a part of an aliphatic ring system as described in U.S. Patent Application Publication No. US 2002/0077487.

Scheme I
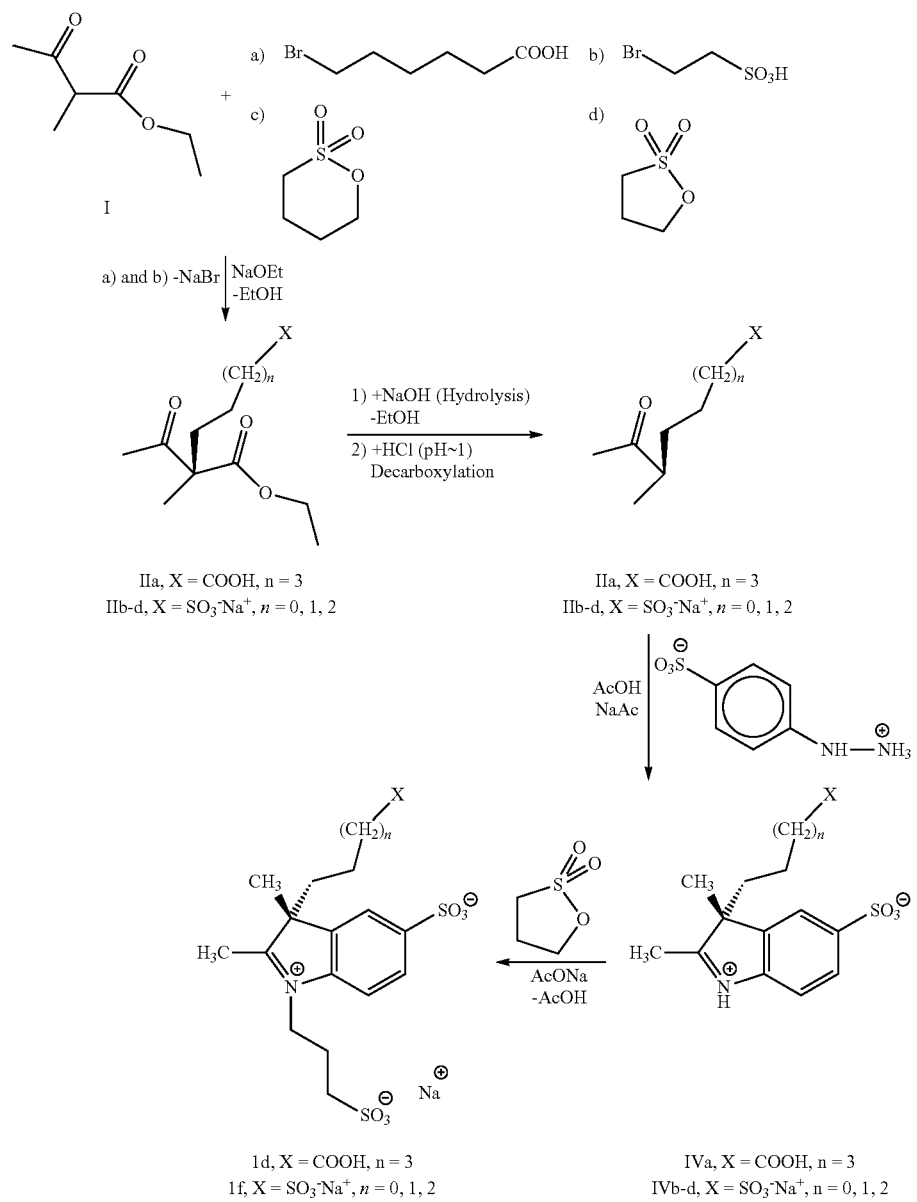
Selected precursor compounds are shown below:
| 1 | $R^1$ | $R^2$ | $R^3$ (y = 2, 3, 4) | $R^4$ |
|---|---|---|---|---|
| a | — | $SO_3^-$ | $CH_3$ | $CH_3$ |
| b | $(CH_2)_5COOH$ | $SO_3K$ | $CH_3$ | $CH_3$ |
| c | $CH_3$ | $SO_3^-$ | $CH_3$ | $CH_3$ |
-continued
| 1 | $R^1$ | $R^2$ | $R^3$ (y = 2, 3, 4) | $R^4$ |
|---|---|---|---|---|
| d | $(CH_2)_3SO_3Na$ | $SO_3^-$ | $(CH_2)_5COOH$ | $CH_3$ |
| e | $(CH_2)_3SO_3Na$ | $SO_3^-$ | $(CH_2)_6OH$ | $CH_3$ |
| f | $(CH_2)_3SO_3Na$ | $SO_3^-$ | $(CH_2)_ySO_3Na$ | $CH_3$ |
| g | $(CH_2)_3SO_3^-$ | $COOH$ | $(CH_2)_5COOH$ | $CH_3$ |

19
-continued

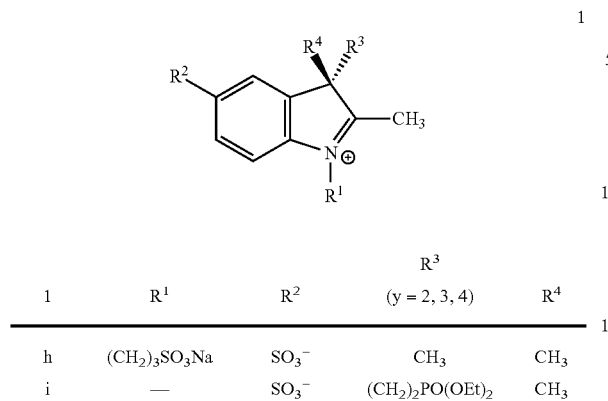

| 1 | R¹ | R² | R³ (y = 2, 3, 4) | R⁴ |
|---|----|----|------------------|-----|
| h | (CH₂)₃SO₃Na | SO₃⁻ | CH₃ | CH₃ |
| i | — | SO₃⁻ | (CH₂)₂PO(OEt)₂ | CH₃ |

EXAMPLE 2

Novel Indolenine Intermediates

Synthesis of 3-(2-phosphonoethyl)-3H-5-indolenines 2,3-dimethyl-3-(2-diethylphosphonatethyl)-3H-5-indolesulfonic acid (1i)

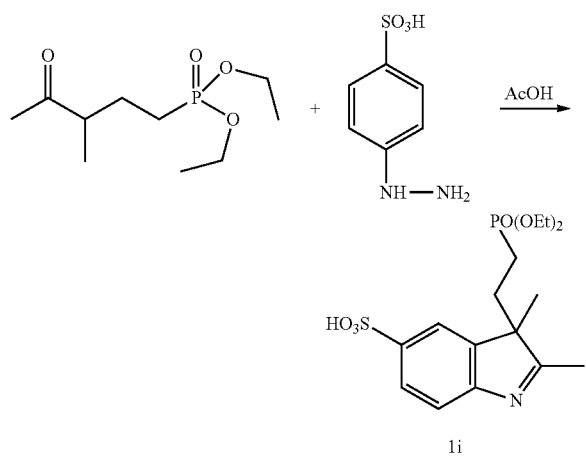

A mixture of 4.70 g (20 mmol) of diethyl 3-methyl-4-oxo-1-butylphosphonate, 3.75 g (20 mmol) of 4-hydrazinobenzenesulfonic acid (synthesis as described above), and 40 ml of acetic acid was refluxed for 20 hours. The insoluble precipitate was filtered and the filtrate was evaporated. The obtained residue was column purified (RP-18, water) to yield 1.27 g (13.7%) of title product as brown sludge oil. $\lambda_{abs}$ 260 nm (water). $\delta_H$ (200 MHz, DMSO-d₆): 7.69 (1H, s, arom H), 7.61 (1H, d, 8.2 Hz, arom H), 7.41 (1H, d, 8.2 Hz arom H), 3.99-3.78 (4H, m, POC$\underline{H}_2$), 2.30 (3H, s, 2-C$\underline{H}_3$), 2.23-1.84 (2H, m, C$\underline{H}_2$) 1.33 (3H, s, 3-C$\underline{H}_3$), 1.24-1.09 (6H, m, CH₂C$\underline{H}_3$), 0.96-0.71 (2H, m, C$\underline{H}_2$).

20
Synthesis of diethyl [2-(2,3,5-trimethyl-3H-indol-3-yl)ethyl]phosphonate (1j)

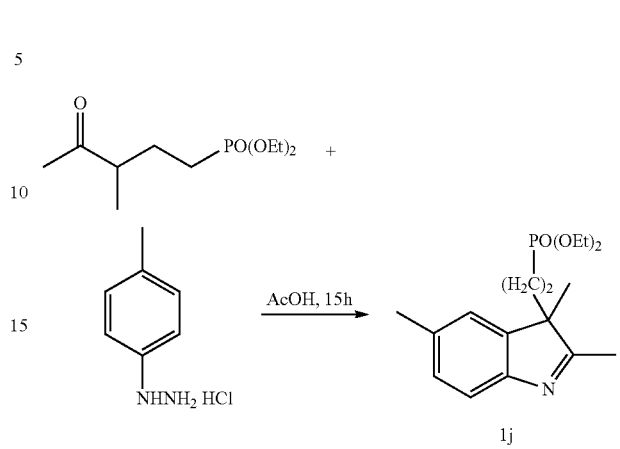

A mixture of 320 mg (2.01 mmol) 3-methyl-4-oxo-1-butylphosphonate, 480 mg (2.01 mmol) (4-methylphenyl)hydrazine hydrochloride and 7 ml acetic acid were refluxed for 15 hours. The solvent was removed under reduced pressure and residue was dried. The product was extracted with ether. Yield: 83%. $\lambda_{abs}$ 275 nm (methanol). $\delta_H$ (200 MHz, DMSO-d₆): 7.31 (1H, d, 8.1 Hz arom H), 7.20 (1H, s, arom H), 7.09 (1H, d, 8.1 Hz arom H), 4.03-3.75 (4H, m, POCH₂), 2.33 (3H, s, 5-CH₃), 2.15 (3H, s, 2-CH₃), 2.07-1.83 (2H, m, CH₂), 1.24 (3H, s, 3-CH₃), 1.16 (6H, t, 7.1 Hz CH₃), 0.90-0.55 (2H, m, CH₂).

Synthesis of diethyl [2-(2,3-dimethyl-3H-indol-3-yl)ethyl]phosphonate (1k)

A mixture of 920 mg (3.89 mmol) 3-methyl-4-oxo-1-butylphosphonate, 560 mg (3.89 mmol) phenylhydrazine hydrochloride and 10 ml acetic acid were refluxed for 5 hours. The solvent was removed under reduced pressure and residue was dried. The product was extracted with ether. Yield: 80% 1k. $\lambda_{abs}$ 257 nm (methanol). $\delta_H$ (200 MHz, DMSO-d₆): 7.48-7.15 (4H, m, arom H), 3.97-3.77 (4H, m, POCH₂), 2.18 (3H, s, 2-CH₃), 2.15-1.80 (2H, m, CH₂), 1.27 (3H, s, 3-CH₃), 1.16 (6H, t, 7.0 Hz CH₃), 1.06-0.56 (2H, m, CH₂).

Synthesis of potassium 2,3-dimethyl-3-(2-phosphonoethyl)-3H-indole-5-sulfonate (1l)

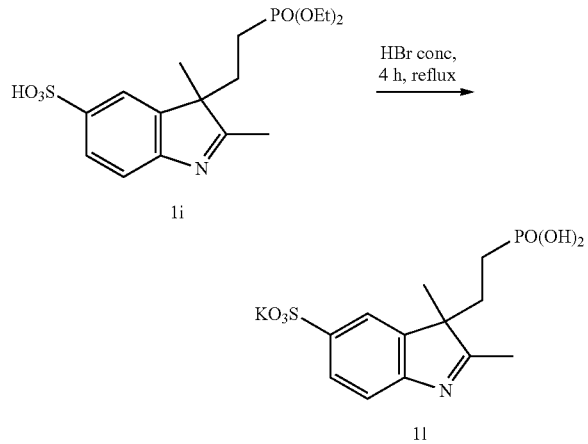

2,3-dimethyl-3-(2-diethylphosphonatethyl)-3H-5-indolesulfonic acid 1i (390 mg, 1 mmol) was dissolved in 5 ml of hydrogen bromide. The mixture was heated at reflux for 4 hours and then cooled to room temperature. Aqueous solution of potassium hydroxide was added slowly until pH 12. The solvent was removed under reduced pressure and residue was column purified (RP-18, water) to give the title product. Yield: 80 mg 1l (21%). $\lambda_{abs}$ 260 nm (water). $\delta_H$ (200 MHz, DMSO-$d_6$): 7.62 (1H, s, arom H), 7.56 (1H, d, 8.2 Hz arom H), 7.32 (1H, d, 8.1 Hz arom H), 2.16 (3H, s, 2-CH$_3$), 2.10-1.77 (2H, m, C$\underline{H}_2$), 1.20 (3H, s, 3-CH$_3$), 0.67-0.31 (2H, m, C$\underline{H}_2$).

Synthesis of di(ethylcarboxypentyloate)[2-(2,3-dimethyl-3H-indol-3-yl)ethyl]phosphonate (1m)

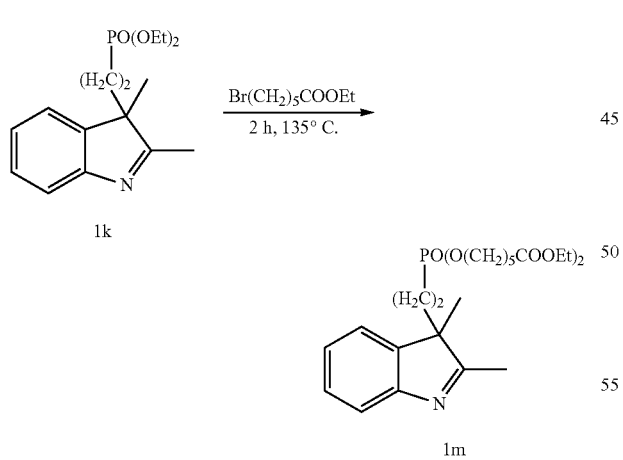

A mixture of 40 mg (0.13 mmol) diethyl [2-(2,3-dimethyl-3H-indol-3-yl)ethyl]phosphonate (1k) and 60 mg (0.27 mmol) ethyl 6-bromohexanoate were heated at 135° C. for 2 hours in argon atmosphere. The product was triturated with hexane, filtered and dried. $\lambda_{abs}$ 278 nm (methanol). $\delta_H$ (200 MHz, DMSO-$d_6$): 7.30-6.54 (4H, m, arom H), 4.15-3.91 (4H, m, POCH$_2$), 3.92-3.62 (4H, m, COCH$_2$), 2.17 (3H, s, 2-CH$_3$), 2.26 (4H, t, 6.8 Hz CH$_2$COOEt), 1.68-1.42 (6H, m, CH$_2$), 1.51 (3H, s, 3-CH$_3$), 1.42-1.53 (8H, m, CH$_2$), 1.23-1.08 (6H, m, CH$_3$), 0.95-0.62 (2H, m, CH$_2$).

Synthesis of di(carboxypentyl)[2-(2,3-dimethyl-3H-indol-3-yl)ethyl]phosphonate (1n)

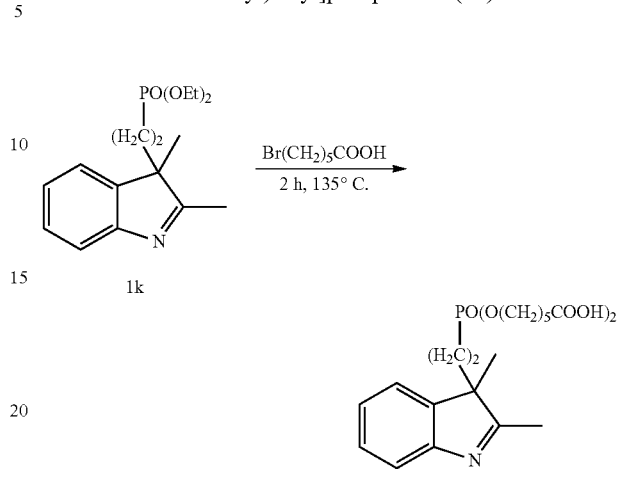

A mixture of 500 mg (1.62 mmol) diethyl [2-(2,3-dimethyl-3H-indol-3-yl)ethyl]phosphonate (1k) and 790 mg (4.04 mmol) bromogexanoic acid were heated at 135° C. for 2 hours in an argon atmosphere. The product was triturated with ether, filtered and dried. Yield: 90% in. $\lambda_{abs}$ 279 nm (methanol). $\delta_H$ (200 MHz, DMSO-$d_6$): 7.26-6.45 (4H, m, arom H), 4.09-3.91 (4H, m, POCH$_2$), 2.19 (4H, t, 6.9 Hz CH$_2$COOH), 2.16 (3H, s, 2-CH$_3$), 1.64-1.40 (6H, m, CH$_2$), 1.52 (3H, s, 3-CH$_3$), 1.40-1.16 (8H, m, CH$_2$), 0.91-0.59 (2H, m, CH$_2$).

Synthesis of dicarboxypenthyl [2-(2,3,5-trimethyl-3H-indol-3-yl)ethyl]phosphonate (1o)

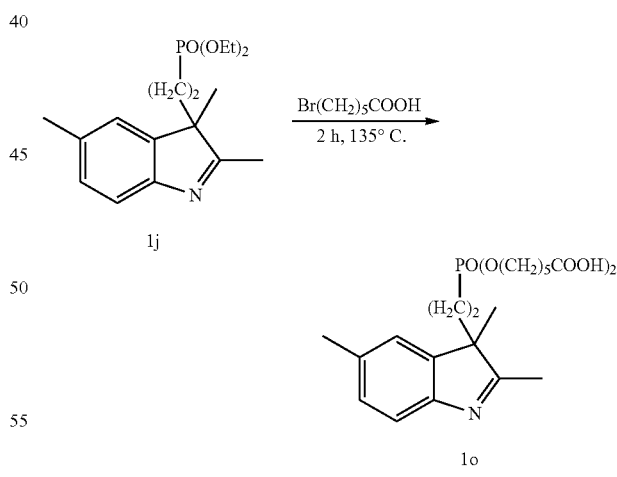

A mixture of 540 mg (1.67 mmol) diethyl [2-(2,3,5-trimethyl-3H-indol-3-yl)ethyl]phosphonate (1j) and 820 mg (4.17 mmol) bromogexanoic acid were heated at 135° C. for 2 hours in argon atmosphere. The product was triturated with ether, filtered and dried. Yield: 71% 1o. $\lambda_{abs}$ 292 nm (methanol). $S_H$ (200 MHz, DMSO-$d_6$): 7.40-6.90 (3H, m, arom H), 3.98 (4H, t, 5.9 Hz POCH$_2$), 2.33-2.12 (10H, m, 5-CH$_3$, 2-CH$_3$, CH$_2$COOH), 1.64-1.39 (10H, m, CH$_2$), 1.52 (3H, s, 3-CH$_3$), 1.39-1.09 (6H, m, CH$_2$).

Synthesis of Potassium 2,3-dimethyl-3-(2-phosphorylethyl)-1-(4-sulfonatobutyl)-3H-5-indoliumsulfonate (1p)

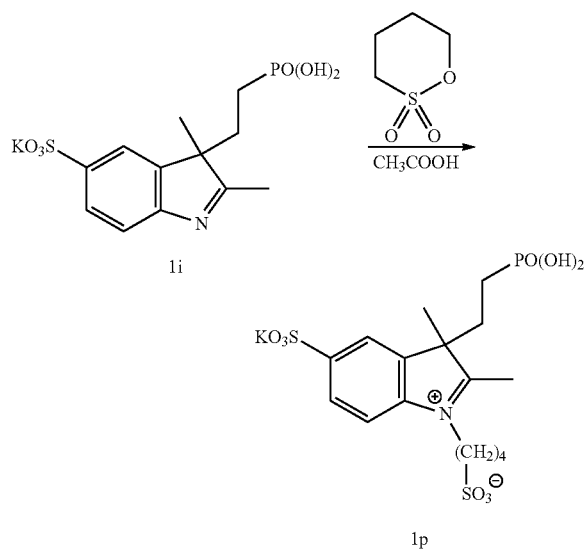

Potassium 2,3-dimethyl-3-(2-phosphonoethyl)-3H-indole-5-sulfonate 1i (100 mg, 0.27 mmol), 1,4-butansulton (0.11 ml, 1.1 mmol) and 0.1 ml of acetic acid were mixed and heated at 150° C. for 5 hours. The raw product was washed with acetone, filtered and dried. Yield: 120 mg (88%) 1p. $\lambda_{abs}$=275 nm. $S_H$ (200 MHz, DMSO-d$_6$): 8.00 (2H, broad s, arom H), 7.85 (1H, d, 7.7 Hz arom H), 4.47 (2H, t, 5.5 Hz, NCH$_2$), 2.85 (3H, s, 2-CH$_3$), 2.55-2.36 (2H, m, CH$_2$SO$_3$H), 2.11-1.87 (2H, m, CH$_2$), 1.83-1.67 (2H, m, CH$_2$), 1.57 (3H, s, 3-CH$_3$), 1.67-1.49 (2H, m, CH$_2$), 1.01-0.68 (2H, m, CH$_2$).

Synthesis of Potassium 2,3-dimethyl-3-[2-(diethylphosphoryl)ethyl]-1-(4-sulfonato butyl)-3H-5-indoliumsulfonate (1q)

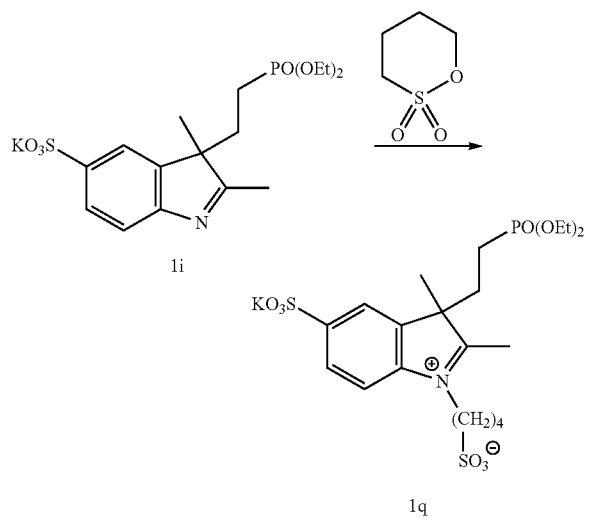

A mixture of potassium 3-[2-(diethoxyphosphoryl)ethyl]-2,3-dimethyl-3H-indole-5-sulfonate 1i (460 mg, 1.08 mmol) and 1,4-butansulton (0.27 ml, 2.7 mmol) was heated at 140° C. for 4 hours. The raw product was triturated with hot 2-propanol, filtered and dried. Then the product was column purified (RP-18, water). Yield: 60 mg (10%) 1q. $\lambda_{abs}$ 276 nm (water). $\delta_H$ (200 MHz, DMSO-d$_6$): 8.04 (1H, s, arom H), 8.01 (1H, d, 7.5 Hz arom H), 7.84 (1H, d, 8.0 Hz arom H), 4.48 (2H, t, 6.6 Hz, NCH$_2$), 4.06-3.81 (4H, m, P(CH$_2$CH$_3$)$_2$), 2.87 (3H, s, 2-CH$_3$), 2.49-2.33 (2H, m, CH$_2$SO$_3$H), 2.02-1.84 (2H, m, CH$_2$), 1.84-1.66 (2H, m, CH$_2$), 1.59 (3H, s, 3-CH$_3$), 1.66-1.50 (2H, m, CH$_2$), 1.26-1.12 (6H, m, P(CH$_2$CH$_3$)$_2$), 0.97-0.74 (2H, m, CH$_2$).

Synthesis of 1-(2-oxyethyl)-2,3-dimethyl-3-[2-(diethylphosphoryl)ethyl])-3H-indole-5-sulfonate (1r)

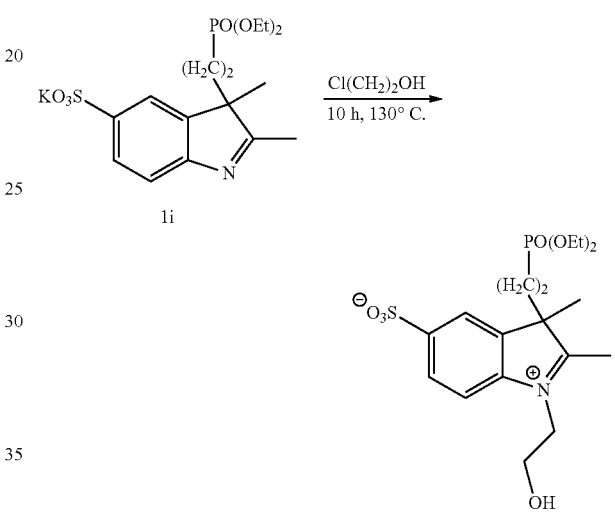

A mixture of potassium 3-[2-(diethoxyphosphoryl)ethyl]-2,3-dimethyl-3H-indole-5-sulfonate (300 mg, 0.7 mmol) and 2-chloroethanol (140 mg, 1.75 mmol) was heated at 130° C. for 10 hours. The raw product was triturated with ether, filtered and dried. $\lambda_{abs}$ 274 nm (water). $\delta_H$ (200 MHz, DMSO-d$_6$): 8.03 (1H, s, arom H), 7.97 (1H, d, 7.5 Hz arom H), 7.83 (1H, d, 8.0 Hz arom H), 4.71-4.53 (2H, m, NCH$_2$), 4.06-3.71 (4H, m, P(CH$_2$CH$_3$)$_2$), 3.64-3.40 (2H, m, CH$_2$), 2.84 (3H, s, 2-CH$_3$), 1.58 (3H, s, 3-CH$_3$), 1.64-1.35 (2H, m, CH$_2$), 1.30-1.01 (6H, m, P(CH$_2$CH$_3$)$_2$), 1.06-1.64 (2H, m, CH$_2$).

Synthesis of dicarboxypenthyl [2-(1-(5-carboxypentyl)-2,3-dimethyl-3H-indoli-3-um)ethyl]phosphonate bromide (1s)

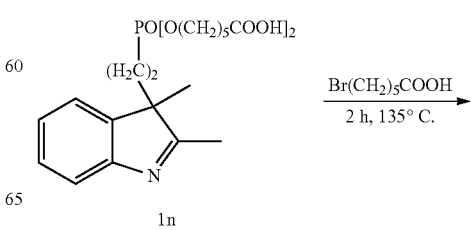

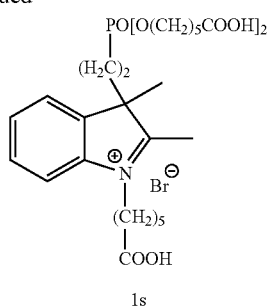

1s

A mixture of 40 mg (0.083 mmol) dicarboxypenthyl [2-(2,3-dimethyl-3H-indol-3-yl)ethyl]phosphonate (1n) and 110 mg (0.166 mmol) bromogexanoic acid were heated at 135° C. for 2 hours in an argon atmosphere. The product was triturated with ether, filtered and dried. $\lambda_{abs}$ 278 nm (methanol). $\delta_H$ (200 MHz, DMSO-$d_6$): 8.08-7.56 (4H, m, arom H), 4.60-4.29 (2H, m, NC$\underline{H}_2$), 4.06-3.81 (4H, m, POC$H_2$), 2.84 (3H, s, 2-C$H_3$), 2.36-2.10 (6H, m, C$H_2$COOH), 1.93-1.68 (4H, m, C$H_2$), 1.68-1.15 (16H, m, C$H_2$), 1.52 (3H, s, 3-C$H_3$), 0.91-0.52 (2H, m, C$H_2$).

Synthesis of Potassium sulfoethyl [2-(1-(2-sulfoethyl)-2,3-dimethyl-3H-indoli-3-um)ethyl]phosphonate bromide (1t)

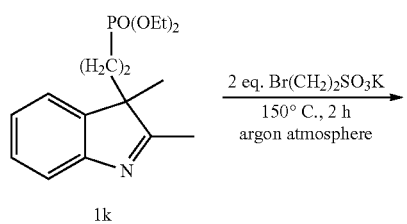

1t

A mixture of indolenine (200 mg, 0.65 mmol) 1k and 2-bromoethansulfonic acid (290 mg, 1.30 mmol) was heated at 150° C. in argon atmosphere for 2 hours. The product was triturated with ether, filtered and dried. Yield: 70%. $\lambda_{abs}$ 275 nm (water). $^1$H NMR (200 MHz, DMSO-$d_6$, ppm): δ 8.10-7.51 (4H, m, arom H), 4.62-4.40 (2H, m, NC$H_2$), 4.14-3.92 (2H, m, POC$H_2$), 2.86 (3H, s, 2-C$H_3$), 2.45-2.13 (4H, m, C$H_2$SO$_3$), 1.64-1.32 (2H, m, C$H_2$), 1.52 (3H, s, 3-C$H_3$), 0.92-0.60 (2H, m, C$H_2$).

Synthesis of Potassium disulfoethyl [2-(1-(2-sulfoethyl)-2,3-dimethyl-3H-indoli-3-um)ethyl]phosphonate bromide (1u)

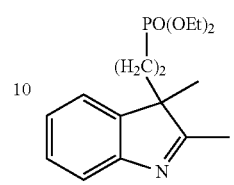

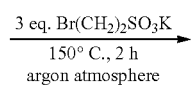

1k

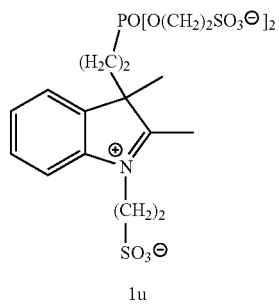

1u

In the same way as above 200 mg (0.65 mmol) of indolenine 1k and 2-bromoethansulfonic acid (440 mg, 1.95 mmol) was heated at 150° C. in argon atmosphere for 2 hours. The product was triturated with ether, filtered and dried. $\lambda_{abs}$ 274 nm (water).

Synthesis of diethyl [2-(1-ethyl-2,3-dimethyl-3H-indoli-3-um)ethyl]phosphonate iodide (1v)

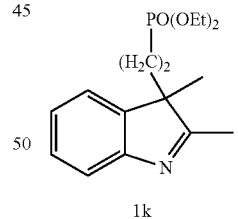

1k

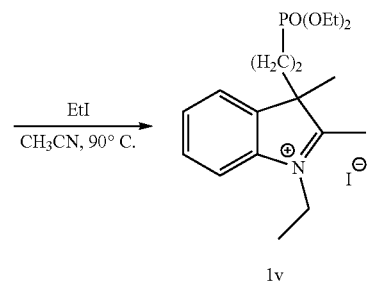

1v

A mixture of 300 mg (0.97 mmol) diethyl [2-(2,3-dimethyl-3H-indol-3-yl)ethyl]phosphonate (1k), 0.5 ml ethyl iodide and 5 ml acetonitryl were heated at 90° C. for 10 hours. The solvent was removed under reduced pressure and residue was dried. Yield: 90% 1v. $\lambda_{abs}$ 279 nm (methanol). $\delta_H$ (200 MHz, DMSO-$d_6$): 8.07-7.61 (4H, m, arom H), 4.51 (2H, q 7.1, 14.5 Hz NC$H_2$), 4.06-3.74 (4H, m, POC$H_2$), 2.87 (3H, s, 2-C$H_3$), 2.46-2.20 (2H, m, C$H_2$), 1.58 (3H, s, 3-C$H_3$), 1.45 (3H, t, 7.2 Hz C$H_2$C$\underline{H}_3$), 1.24-1.11 (6H, m, PO(CH$_2$C$\underline{H}_3$)$_2$), 0.95-0.72 (2H, m, C$H_2$).

Synthesis of 1-(5-carboxypentyl)-3,3-dimethyl-2-[(1E,3E)-4-(phenylamino)buta-1,3-dien-1-yl]-3H-indolium bromide

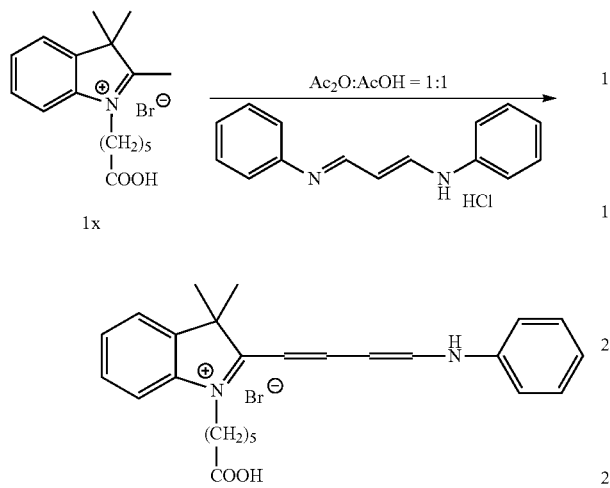

A mixture of indolenine derivative 1x (500 mg, 1.41 mmol), malondialdehyde-bis-(phenylimin) monohydrochloride (550 mg, 2.11 mmol), 5 ml of acetic acid and 5 ml of acetic anhydride were heated at reflux for 4 hours. The solvent was removed under reduced pressure and residue was triturated with ether. Yield: quantitative. $\lambda_{abs}$ 446 nm (methanol).

Synthesis of 1-(5-carboxyypentyl)-3,3-dimethyl-2-[(E)-2-(phenylamino)ethenyl]-3H-indolium-5-sulfonate

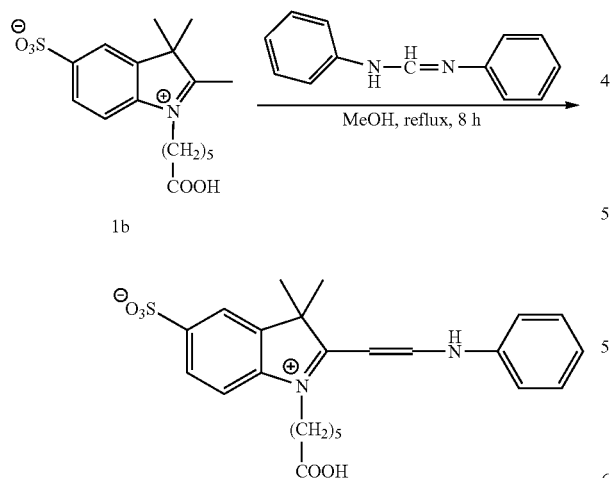

A mixture of indolenine derivative 1b, N,N'-diphenylimidoformamide and methanol were heated at reflux for 8 hours. The solvent was removed under reduced pressure until dry and residue was triturated with ethyl acetate. The product was filtrated and dried. Yield: 90%. $\lambda_{abs}$ 415 nm (water).

Synthesis of dipotassium 2,3-dimethyl-1,3-di(4-sulfonatobutyl)-3H-5-indolium sulfonate (1y)

Synthesis of 5-ethyloxycarbonyl-5-methyl-6-oxo-1-heptanesulfonic acid

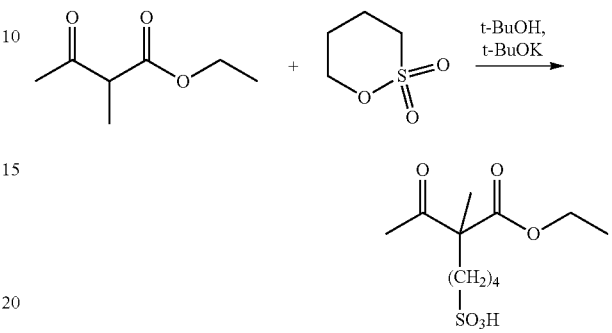

0.35 ml (3.47 mmol) of 1,4-butane sultone were added to a mixture of 0.49 ml (3.47 mmol) ethyl 2-methylacetoacetate and 513 mg (4.2 mmol) of tert-BuOK in 12 ml tert-butanol and refluxed for 15 hours. The formed precipitate was filtered and washed with hexane to yield 730 mg of 5-ethyloxycarbonyl-5-methyl-6-oxo-1-heptanesulfonic acid. $\delta_H$ (200 MHz, DMSO-$d_6$): 4.12 (2H, q, 7.1, 14.2 Hz, OC$\underline{H}_2$), 3.97 (2H, t, 5.8 Hz, C$\underline{H}_2$SO$_3$H), 2.10 (3H, s, COC$\underline{H}_3$), 1.78-1.41 (4H, m, C$\underline{H}_2$), 1.24-1.01 (2H, m, C$\underline{H}_2$), 1.22 (3H, s, CC$\underline{H}_3$), 1.17 (3H, t, 7.3 Hz, CH$_2$C$\underline{H}_3$).

Synthesis of 2,3-dimethyl-3-(4-sulfobutyl)-3H-5-indolesulfonic acid (IVd)

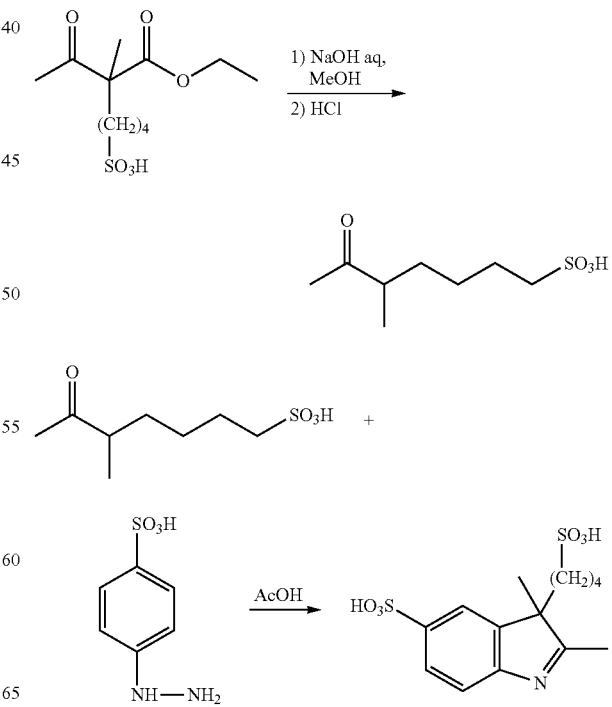

A solution of 290 mg of NaOH in 3 ml water was added to the mixture of 710 mg (2.53 mmol) of 5-ethyloxycarbonyl-5-methyl-6-oxo-1-heptanesulfonic acid in 15 ml of methanol. The obtained mixture was stirred for 15 hours at 50° C. Methanol was removed by a rotary evaporator, residue was acidified to pH 1 and then solvent was removed until dry to yield 5-methyl-6-oxo-1-heptanesulfonic acid. The product thus obtained (940 mg, 4.5 mmol), 1.02 g (5.4 mmol) of 4-hydrazinobenzenesulfonic acid, and 15 ml of acetic acid was refluxing for 16 hours. The insoluble precipitate was filtered and the filtrate was evaporated. The obtained residue was column purified (RP-18, water) to yield 840 mg of the 2,3-dimethyl-3-(4-sulfobutyl)-3H-5-indolesulfonic acid (IVd). $\delta_H$ (200 MHz, DMSO-$d_6$): 7.66 (1H, s, arom H), 7.6 (1H, d, 8.0 Hz, arom H), 7.4 (1H, d, 7.8 Hz arom H), 2.66 (2H, t, 6.8 Hz, C$\underline{H}_2$SO$_3$H), 2.32 (3H, s, 2-C$\underline{H}_3$), 2.10-1.78 (2H, m, C$\underline{H}_2$), 1.53-1.26 (2H, m, C$\underline{H}_2$), 1.31 (3H, s, 3-C$\underline{H}_3$), 0.83-0.41 (2H, m, C$\underline{H}_2$).

Synthesis of dipotassium 2,3-dimethyl-1,3-di(4-sulfonatobutyl)-3H-5-indoliumsulfonate (1y)

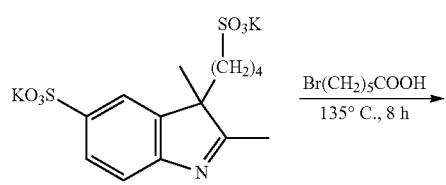

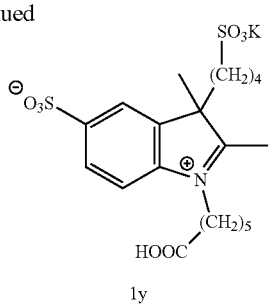

A mixture of dipotassium 2,3-dimethyl-3-(4-sulfonatobutyl)-3H-indole-5-sulfonate (1.96 g, 4.72 mmol) and 6-bromohexanoic acid (2.3 g, 11.79 mmol) was heated at 135° C. for 8 hours under argon atmosphere. The raw product was column purificated (RP-18, water) to yield the title product as beige powder. Yield: 40% 1y. $\lambda_{max}$ Ab 275 nm (water). $\delta_H$ (200 MHz, DMSO-$d_6$): 7.99 (1H, s, arom H), 7.94 (1H, d, 8.2 Hz, arom H), 7.83 (1H, d, 8.2 Hz, arom H), 4.47 (2H, t, 7.1 Hz, NC$\underline{H}_2$), 2.87 (3H, s, 2-C$\underline{H}_3$), 2.38-2.15 (2H, m, C$\underline{H}_2$SO$_3$H), 2.23 (2H, t, 7.1 Hz, C$\underline{H}_2$COOH), 1.92-1.74 (2H, m, C$\underline{H}_2$), 1.64-1.32 (8H, m, C$\underline{H}_2$), 1.53 (3H, s, 3-C$\underline{H}_3$), 0.86-0.42 (2H, m, C$\underline{H}_2$)

Other important intermediates for the synthesis of cyanine dyes are described in Mujumdar et al., Bioconjugate Chem. 4(2) 105-111, 1993 and in several other patent applications (U.S. Patent Appl. US 2002/0077487 A1, U.S. Pat. No. 5,569,587, U.S. Pat. No. 5,672,027, U.S. Pat. No. 5,808,044 and WO 2005/044923).

EXAMPLE 3

Synthesis of 3-[2-(diethylphosphoryl)ethyl]-3H-indolenine cyanine 2

A mixture of 4-[2-(-4-anilino-1,3-butadienyl)-3-(5-carboxypentyl)-3-methyl-5-sulfo-3H-1-indoliumyl]-1-butanesulfonate (270 mg, 0.42 mmol) synthesized according to Mujumdar et al., Bioconjugate Chem. 4(2) 105-111, 1993, and indolenine derivative 1q (197 mg, 0.35 mmol), 7 ml of dry pyridine and 7 ml of acetic anhydride were heated at reflux for min. The solvent was removed under reduced pressure until dry. The raw product was column purified (RP-18, water) to give the title dye as blue powder. $\lambda_{abs}$ 651 nm, $\lambda_{em}$ 671 nm (water). $\delta_H$ (200 MHz, DMSO-$d_6$): 8.50-8.28 (2H, m, βH), 7.82 (2H, s, arom H), 7.63 (2H, d, 8.4 Hz arom H), 7.35 (2H, d, 8.4 Hz, arom H), 6.61 (1H, t, 12.2 Hz, γH), 6.42 (1H, d, 13.6 Hz, αH), 6.37 (1H, d, 13.5 Hz, αH), 4.19-3.96 (4H, m, NC$\underline{H}_2$), 3.88-3.65 (4H, m, P(C$\underline{H}_2$CH$_3$)$_2$), 2.59-2.42 (2H, m, C$\underline{H}_2$SO$_3$H), 2.19 (2H, t, 7.0 Hz, C$\underline{H}_2$COOH), 1.72 (3H, s, 3-CH$_3$), 1.69 (6H, s, 3-CH$_3$), 1.80-1.60 (6H, m, C$\underline{H}_2$), 1.60-1.46 (4H, m, C$\underline{H}_2$), 1.44-1.32 (2H, m, C$\underline{H}_2$), 1.20-1.03 (2H, m, C$\underline{H}_2$), 1.19-1.07 (6H, m, P(CH$_2$C$\underline{H}_3$)$_2$), 0.87-0.53 (2H, m, C$\underline{H}_2$).

EXAMPLE 4

Synthesis of
3-[2-(diethylphosphoryl)ethyl]-3H-indolenine
cyanine 3

2-(4-anilino-1,3-butadienyl)-1-(5-carboxypentyl)-3-methyl-3-(4-sulfobutyl)-3H-5-indoliumsulfonate

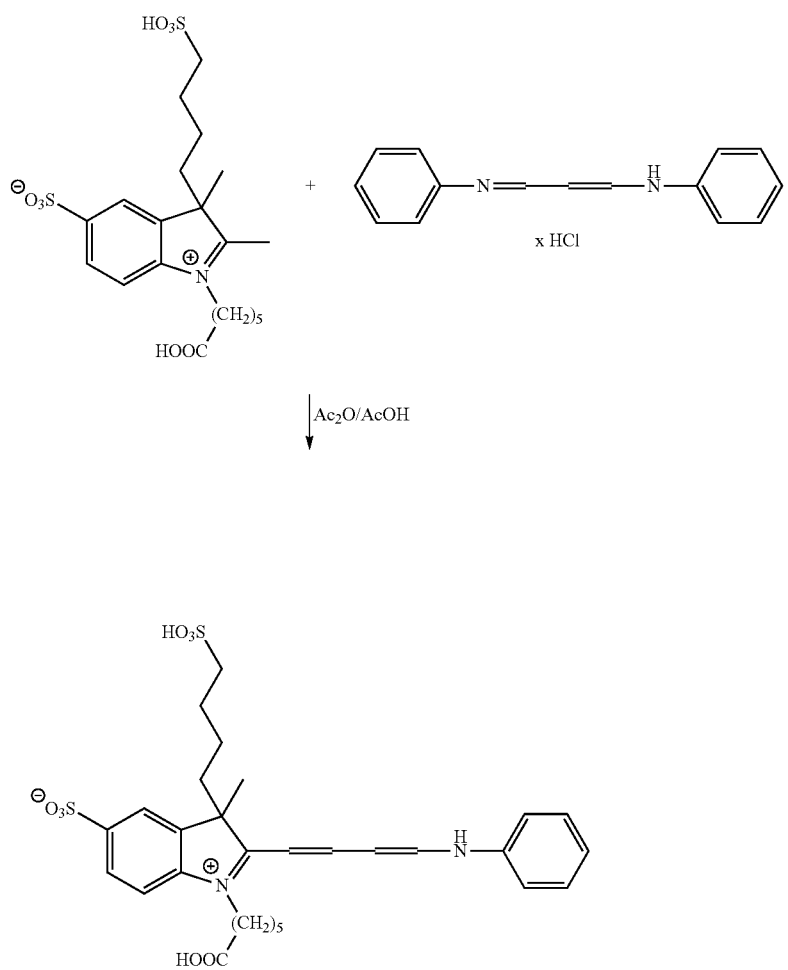

A mixture of 500 mg (0.973 mmol) of indolenine 1y and 503 mg (1.946 mmol) of malondialdehyde-bis-(phenylimin) monohydrochloride (Sigma-Aldrich, Cat.: 38, 353-8, Lot.: S47683-178) were refluxed with stirring for 4.5 h. After cooling to RT 2.7 mL water were added, which was accompanied with spontaneous heating. The solvent was removed under reduced pressure and the residue was treated with 40 mL of ethylacetate. The oily solid was filtered off, washed with ethyl acetate until the solvent became colorless and dried over $P_2O_5$. The yield was almost quantitative. UV: Absorption 453 nm (water).

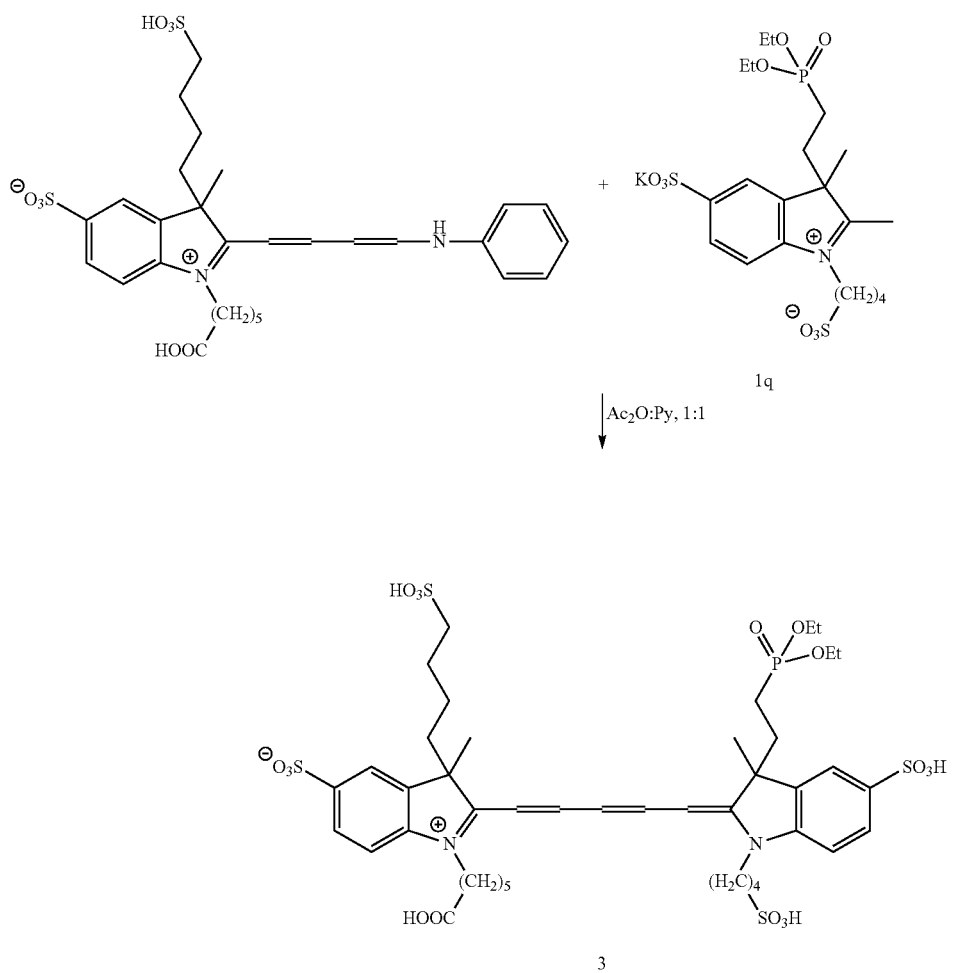

Dye 3 was obtained from 2-(4-anilino-1,3-butadienyl)-1-(5-carboxypentyl)-3-methyl-3-(4-sulfobutyl)-3H-5-indoliumsulfonate and indolenine derivative 1q analogously to dye 2. $\lambda_{abs}$=654 nm, $\lambda_{em}$=671 nm. $\delta_H$ (200 MHz, DMSO-$d_6$): 8.50-8.29 (2H, m, 13 H), 7.80 (2H, s, arom H), 7.64 (2H, d, 8.2 Hz arom H), 7.34 (2H, d, 8.2 Hz, arom H), 6.61 (1H, t, 12.2 Hz, γH), 6.40 (2H, d, 13.6 Hz, αH), 4.20-3.96 (4H, m, NCH_2), 3.95-3.61 (4H, m, P(CH_2CH_3)_2), 2.34-2.14 (4H, m, CH_2SO_3H), 2.19 (2H, t, 7.1 Hz, CH_2COOH), 1.73 (3H, s, 3-CH_3), 1.66 (3H, s, 3-CH_3), 1.81-1.60 (6H, m, CH_2), 1.60-1.30 (8H, m, CH_2), 1.26-1.05 (2H, m, CH_2), 1.20-1.06 (6H, m, P(CH_2CH_3)_2), 0.87-0.42 (4H, m, CH_2).

EXAMPLE 5

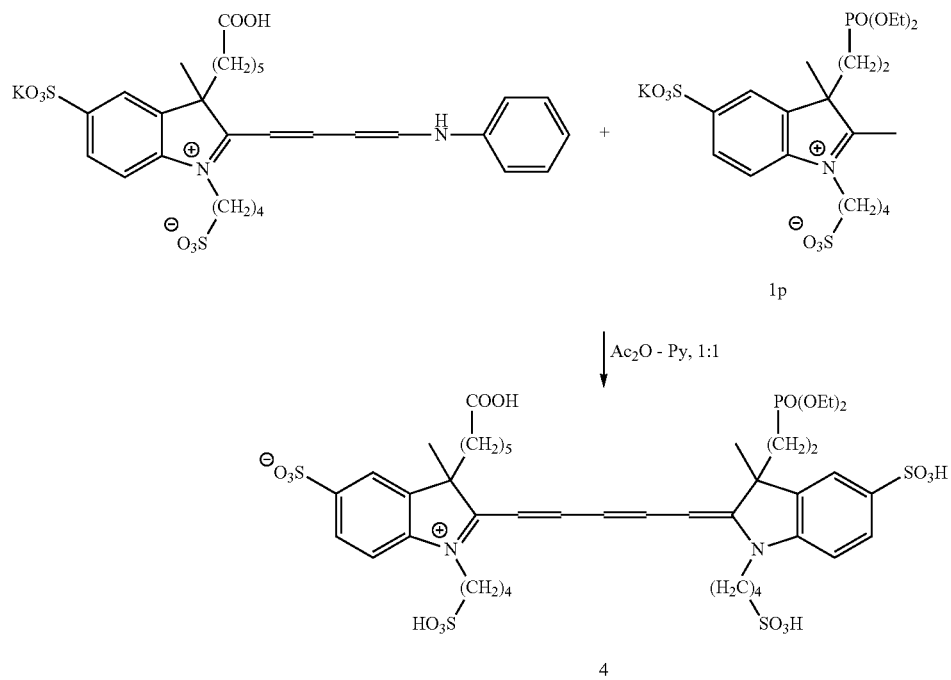

Dye 4 was obtained from potassium 2-(4-anilino-1,3-butadienyl)-3-(5-carboxypentyl)-3-methyl-1-(4-sulfonatobutyl)-3H-5-indoliumsulfonate and indolenine derivative 1p analogously to the procedure described in Example 3.

Compound 4: $\delta_H$ (200 MHz, DMSO-$d_6$): 8.48-8.26 (2H, m, 3H), 7.76 (2H, s, arom H), 7.64 (2H, d, 7.7 Hz arom H), 7.38 (2H, d, 7.8 Hz, arom H), 6.61 (1H, t, 12.3 Hz, γH), 6.47 (1H, d, 12.8 Hz, αH), 6.39 (1H, d, 12.1 Hz, αH), 4.19-4.03 (4H, m, NC$\underline{H}_2$), 4.96-3.81 (4H, m, P(C$\underline{H}_2$CH$_3$)$_2$), 2.6-2.26 (4H, m, C$\underline{H}_2$SO$_3$H), 2.04 (2H, t, 6.7 Hz, C$\underline{H}_2$COOH), 1.72 (3H, s, 3-CH$_3$), 1.67 (3H, s, 3-CH$_3$), 1.88-1.42 (10H, m, C$\underline{H}_2$), 1.39-0.92 (6H, m, C$\underline{H}_2$), 1.12 (6H, t, 6.9 Hz, P(CH$_2$C$\underline{H}_3$)$_2$), 0.89-0.28 (4H, m, C$\underline{H}_2$).

EXAMPLE 6

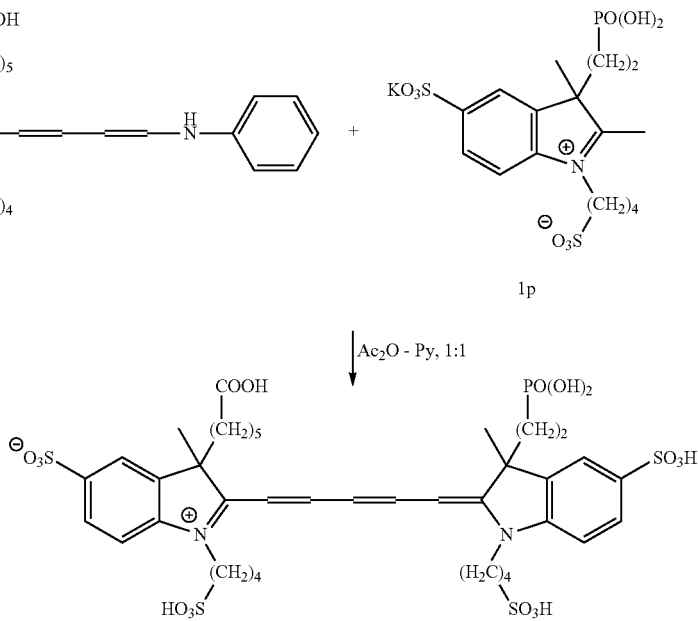

Dye 5 was obtained from potassium 2-(4-anilino-1,3-butadienyl)-3-(5-carboxypentyl)-3-methyl-1-(4-sulfonatobutyl)-3H-5-indoliumsulfonate and potassium 2,3-dimethyl-3-(2-phosphorylethyl)-1-(4-sulfonatobutyl)-3H-5-indoliumsulfonate (1p) analogously to the procedure given for Example 3.

Compound 5: $\lambda_{abs}$=653 nm, $\lambda_{em}$=672 nm (water). $\delta_H$ (200 MHz, DMSO-$d_6$): 8.40-8.18 (2H, m, βH), 7.75 (1H, s, arom H), 7.71 (1H, s, arom H), 7.63 (2H, d, 8.5 Hz arom H), 7.33 (2H, d, 7.8 Hz, arom H), 6.61 (1H, t, 12.3 Hz, γH), 6.46 (1H, d, 13.0 Hz, αH), 6.40 (1H, d, 12.5 Hz, αH), 4.19-4.03 (4H, m, NC$\underline{H}_2$), 2.59-2.27 (4H, m, C$\underline{H}_2$SO$_3$H), 2.05 (2H, t, 7.4 Hz, C$\underline{H}_2$COOH), 1.72 (3H, s, 3-CH$_3$), 1.66 (3H, s, 3-CH$_3$), 1.89-1.52 (6H, m, C$\underline{H}_2$), 1.42-0.99 (10H, m, C$\underline{H}_2$), 0.95-0.35 (4H, m, C$\underline{H}_2$).

EXAMPLE 7

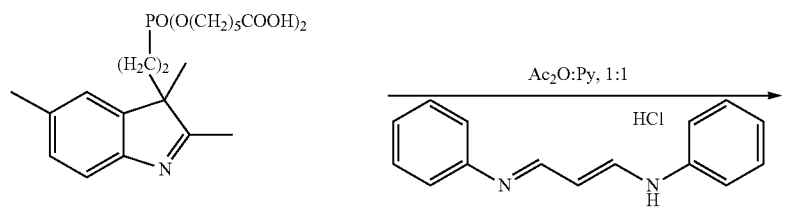

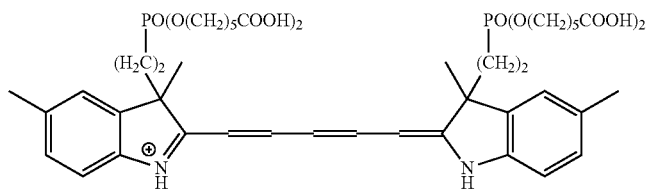

6

A mixture of indolenine derivative 1n (590 mg, 1.14 mmol), malondialdehyde-bis-(phenylimin) monohydrochloride (120 mg, 0.46 mmol), 10 ml of dry pyridine and 10 ml of acetic anhydride were heated at reflux for min. The solvent was removed under reduced pressure until dry. The raw product was column purified (RP-18, CH$_3$CN—H$_2$O:60-80%) to give the dye as blue resin. $\lambda_{abs}$ 667 nm, $\lambda_{em}$ 685 nm (chloroform). $\delta_H$ (200 MHz, DMSO-$d_6$): 8.28 (2H, t, 13.1 Hz βH), 7.41 (2H, s, arom H), 7.33-7.15 (4H, m, arom H), 6.55 (1H, t, 12.2 Hz γH), 6.30 (2H, d, 13.6 Hz αH), 3.98 (8H, t, 5.8 Hz POCH$_2$), 2.37 (3H, s, 5-CH$_3$), 2.27 (3H, s, 5-CH$_3$), 2.41-2.11 (8H, m, CH$_2$COOH), 1.82-0.93 (28H, m, CH$_2$), 1.53 (6H, s, 3-CH$_3$), 0.81-0.42 (4H, m, CH$_2$).

EXAMPLE 8

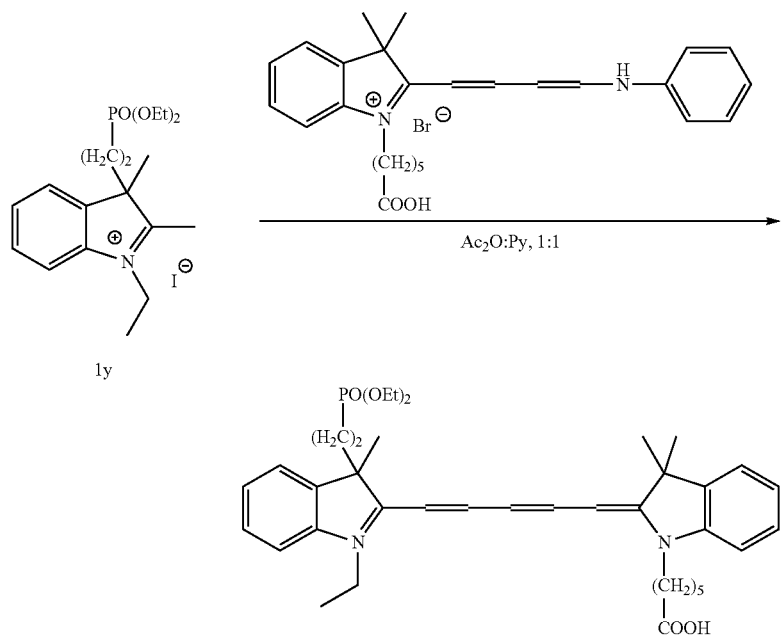

The dye was obtained from indolenine derivative 1y and 1-(5-Carboxypentyl)-3,3-dimethyl-2-[(E)-2-(phenylamino) ethenyl]-3H-indolium-5-sulfonate (see above) analogously to dye 7. The raw product was column purified (Silica gel 60, MeOH—CHCl$_3$, 15%) to give the dye as blue resin. $\lambda_{abs}$ 661 nm, $\lambda_{em}$ 682 nm (chloroform). $\delta_H$ (200 MHz, DMSO-d$_6$): 8.50-8.27 (1H, m, βH), 7.64 (2H, s, arom H), 7.42 (2H, d, 7.1 Hz, arom H), 7.28 (2H, d, 7.2 Hz, arom H), 6.60 (1H, t, 12.1 Hz, γH), 6.37 (1H, d, 13.9 Hz, αH), 6.33 (1H, d, 13.6 Hz, αH), 4.25-4.03 (4H, m, NCH$_2$), 3.97-3.73 (4H, m, POCH$_2$), 2.20 (2H, t, 7.4 Hz, CH$_2$COOH), 1.73 (3H, s, 3-CH$_3$), 1.72 (3H, s, 3-CH$_3$), 1.69 (6H, s, 3-CH$_3$), 1.81-1.31 (8H, m, CH$_2$), 1.25 (3H, t, 6.7 Hz, CH$_3$), 1.19-1.06 (6H, m, CH$_3$), 0.89-0.53 (2H, m, CH$_2$).

EXAMPLE 9

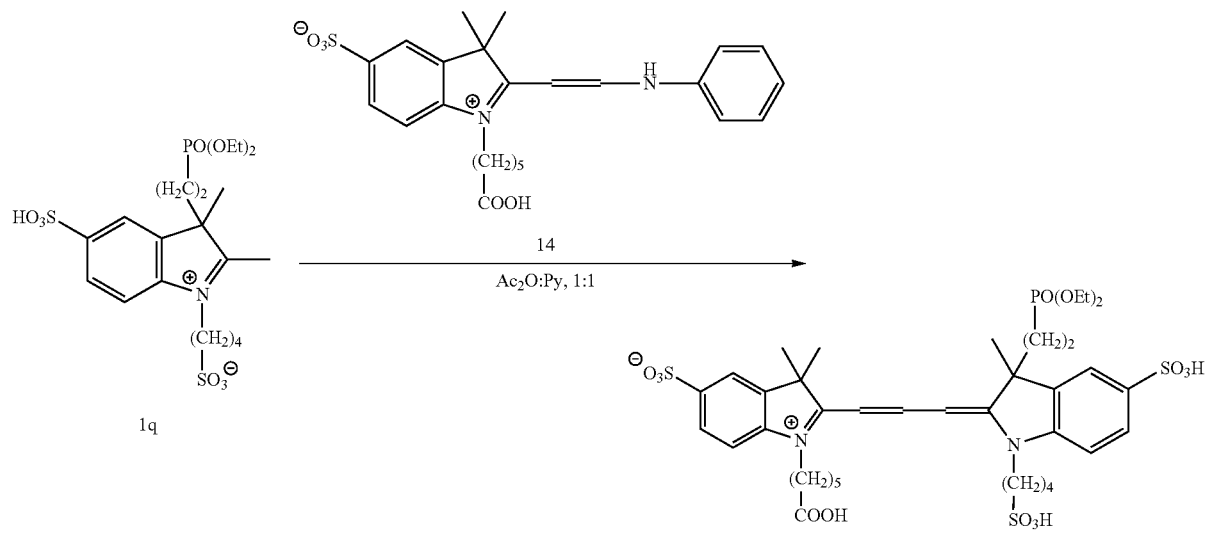

The dye was synthesized from indolenine derivative 1q and 1-(5-Carboxypentyl)-3,3-dimethyl-2-[(E)-2-(phenylamino)ethenyl]-3H-indolium-5-sulfonate (see above) analogously to Example 3. The raw product was column purified (RP-18, CH$_3$CN—H$_2$O, 10%) to give the dye as purple powder. Yield: 5% 8. $\lambda_{abs}$ 556 nm, $\lambda_{em}$ 570 nm (water). $\delta_H$ (200 MHz, DMSO-d$_6$): 8.31 (1H, t, 13.0 Hz, βH), 7.81 (2H, s, arom H), 7.69 (2H, d, 7.9 Hz arom H), 7.46 (1H, d, 7.1 Hz, arom H), 7.42 (1H, d, 7.3 Hz, arom H), 6.60 (2H, d, 13.3 Hz, αH), 4.23-4.04 (4H, m, NCH$_2$), 3.96-3.77 (4H, m, POCH$_2$), 2.67-2.53 (2H, m, CH$_2$SO$_3$H), 2.23 (2H, t, 6.7 Hz, CH$_2$COOH), 1.73 (3H, s, 3-CH$_3$), 1.71 (6H, s, 3-CH$_3$), 1.88-1.64 (6H, m, CH$_2$), 1.64-1.32 (6H, m, CH$_2$), 1.13 (6H, t, 7.0 Hz, CH$_3$), 0.98-0.68 (2H, m, CH$_2$).

EXAMPLE 10

Synthesis of Cyanine Dyes Having a Spacer Group in the Conjugated Chain 2-carboxymethylsulfanyl-3-phenylimino-1-propenyl (phenyl)ammonium bromide

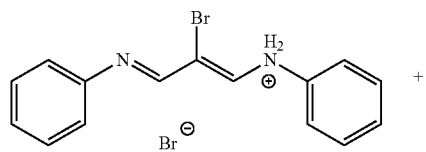 +

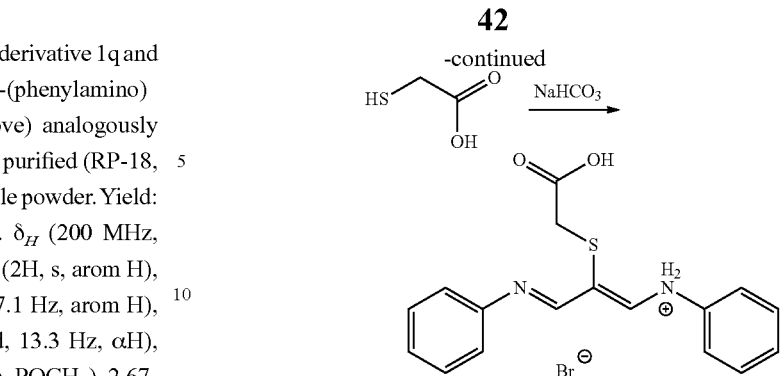

A mixture of 560 mg (1.85 mmol) of 2-mercaptoacetic acid and 345 mg (4.1 mmol) of NaHCO$_3$ in 3 mL water was heated with stirring at 60° C. for 1 h. Then a solution of 573 mg (1.5 mmol) of 2-bromo-3-phenylimino-1-propenyl(phenyl)ammonium bromide (synthesized as described in EP1221465A1) in 20 mL of methanol was added at 60° C., the mixture was stirred at this temperature for 5 h, cooled to RT, poured into a mixture of 50 g of ice and 1 mL of concentrated hydrochloric acid. The obtained yellow precipitate was filtered and dried.

Dye 9

A mixture of 113 mg (0.2 mmol) of indolenine 1q and 39 mg (0.1 mmol) of 2-carboxymethylsulfanyl-3-phenylimino-1-propenyl(phenyl)ammonium bromide was refluxed with stirring for 4 h in a mixture of 3 mL acetic anhydride and 3 ml pyridine. The solvent was evaporated under a reduced pressure and the product was column purified (Silica gel RP-18). Compound 9: $\lambda_{abs}$=645 nm, $\lambda_{em}$=666 nm (water).

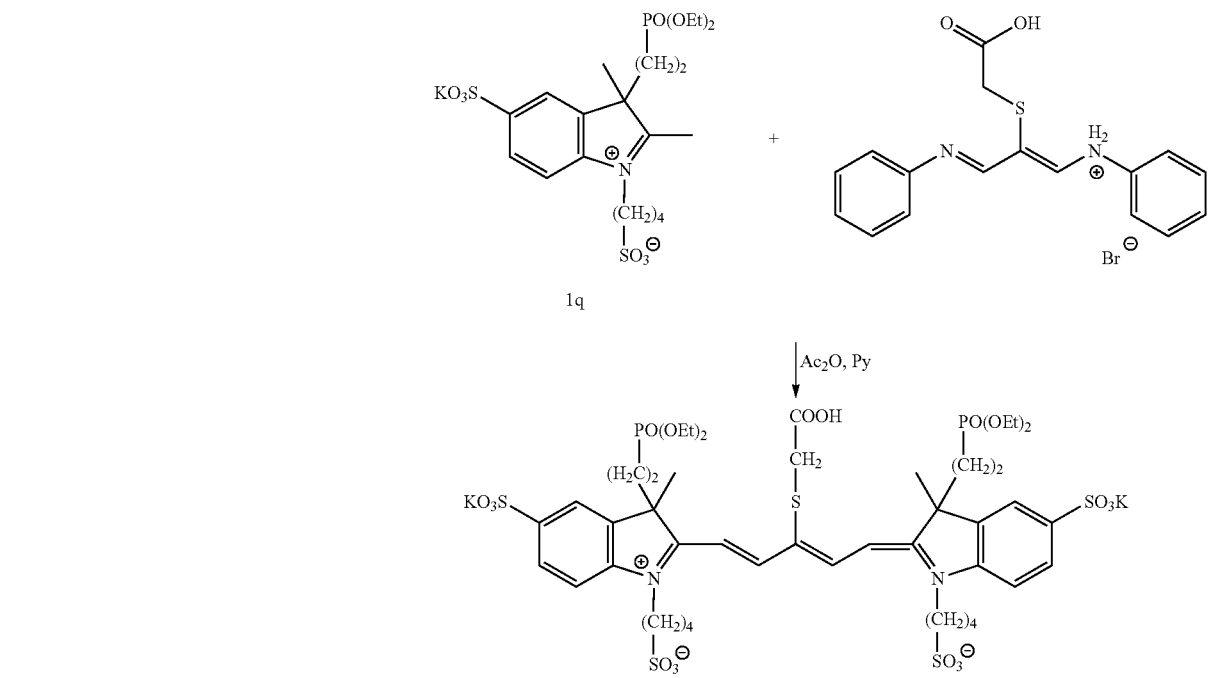

EXAMPLE 11

Synthesis of the symmetrical heptamethin-cyanine 10

Glutaconaldehyde bis(phenylimine) hydrochloride (143 mg, 0.5 mmol) is dissolved in a hot mixture of acetic anhydride (4 mL) and 1 mL of pyridine and 1 mmol of 1r is added and the mixture is heated for an additional minutes and then cooled. The solvent was removed under reduced pressure until dry. Raw product was column purified (RP-18, water) to give the title compound 10.

Synthesis of the sulfo-phenoxy compound (12)

A cooled suspension (0° C.) of 60% of sodium hydride (120 mg, 3 mmol of 100% NaH) in 10 mL of dry DMF is added to a cooled DMF solution of 4-hydroxybenzene sulfonic acid dihydrate (2 mmole) under nitrogen atmosphere. After about min the reaction temperature is increased to RT and after 20 min at RT the mixture is transferred into a flask containing the chloro-dye 11 (1 mmol) in 30 mL of DMF and the solution is vigorously stirred at RT for about min to 1 h. The reaction mixture is quenched with dry ice and the DMF was removed under reduced pressure. The crude product was purified by reversed phase C-18 column chromatography using water as eluent.

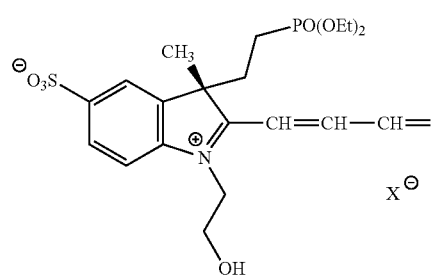

10

EXAMPLE 12

Synthesis of the sulfo-phenoxy compounds (12)

Synthesis of chloro-dye precusor (11)

A mixture of 5 mmols of 1q, and 1y, N-[(3-anilinoethylene)-2-chloro-1-cyclohexene-1-yl)-methylene]aniline monohydro-chloride (1.30 g, 5 mmol) and sodium acetate (1.1 g, 13 mmol) is refluxed in 30 mL of dry ethanol for 1 h. Subsequently the reaction is cooled to RT and the solvent is removed under reduced pressure and the residue is purified by reversed phase C-18 column chromatography using methanol-water mixtures as eluent.

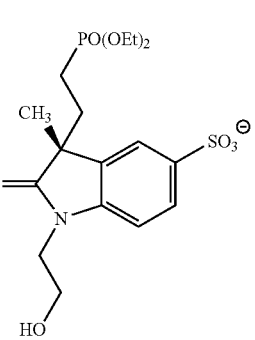

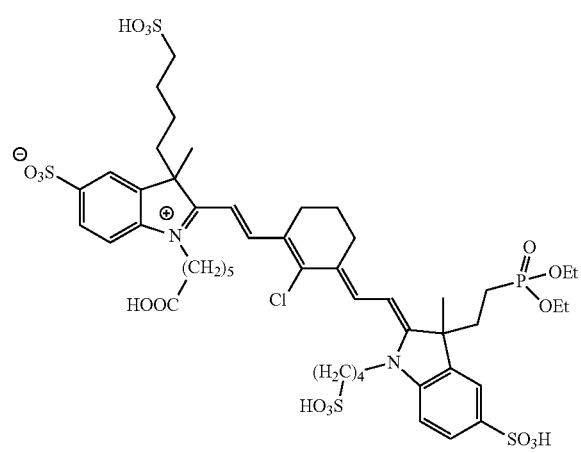

11

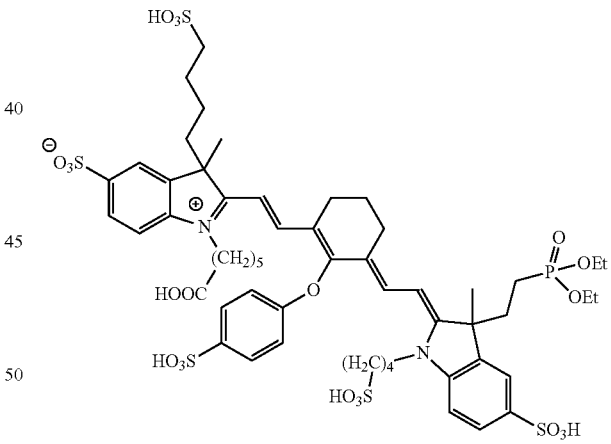

12

EXAMPLE 13

Synthesis of NHS-esters a) With TSTU (N,N,N',N'-Tetramethyl(Succinimido)Uronium Tetrafluoro Borate)

26 μl (0.15 mmol) of diisopropylethylamine and 38 mg (0.6 mmol) of TSTU are added to a mixture of 0.05 mmol 3 in 1 mL of DMF, 1 mL of dioxane, and 0.5 mL of water. After min, the mixture is filtered, and the solvents are removed in vacuum. The product is dried over $P_2O_5$ and used without further purification.

b) With NHS/DCC 1 mL of anhydrous DMF is added to a mixture of 0.023 mmol of 4, 14 mg (0.069 mmol) of dicyclohexylcarbodiimide (DCC), and 8 mg (0.069 mmol) of N-hydroxysuccinimide (NHS). The solution is stirred for 24 h at room temperature and then filtered. The solvent is removed in vacuum, and the product is triturated with ether and dried over $P_2O_5$.

EXAMPLE 14

General Protein Labelling Procedures and Determination of Dye-to-Protein Ratios

Protein labelling reactions are carried out using a 50 mM bicarbonate buffer (pH 9.1). A stock solution of 1 mg of dye in 100 µL of anhydrous DMF is prepared. 10 mg of protein is dissolved in 1 mL of 100 mM bicarbonate buffer (pH 9.1). Dye from the stock solution is added, and the mixture is stirred for 8-12 h at room temperature.

Unconjugated dye is separated from labeled protein using gel permeation chromatography with SEPHADEX G50 (0.5 cm×20 cm column) and a 22 mM phosphate buffer solution (pH 7.3) as the eluent. The first colored band contains the dye-protein conjugate. The blue band with the much higher retention time contains the separated free dye. A series of labeling reactions using different dye-to-protein starting ratios are set up to obtain different dye-to-protein ratios for the labeled protein.

The protein concentrations are determined using the BCA Protein Assay Reagent Kit from Pierce (Rockford, Ill.). The dye-to-protein ratio (D/P) gives the number of dye molecules covalently bound to protein.

Covalent Attachment of 4—NHS-Ester to Polyclonal Anti-HSA

385 µL (5.2 mg/mL) of anti-HSA is dissolved in a 750 µL bicarbonate buffer (0.1 M, pH 9.0). 1 mg of NHS-ester of dye 4 is dissolved in 50 µL of DMF and slowly added to the above-prepared protein solution with stirring. After 20 h of stirring, the protein-conjugate is separated from the free dye using Sephadex G50 and a phosphate buffer (22 mM, pH 7.2). The first blue band that is isolated contains the labeled conjugate.

Conjugation of 3—NHS to HSA 0.5 mg of the NHS ester of dye 3 in 50 µL of DMF are slowly added to a stirred solution of 5 mg of HSA in 750 µL of bicarbonate buffer (0.1 M, pH 9.0). The mixture is stirred for another 6 h at room temperature. The mixture is dialyzed against a phosphate buffer (22 mM, pH 7.2) using a dialysis membrane (1500 FT, Union Carbide) with a cutoff of 10.000.

The labeling procedures of alternative reporter compounds having reactive functional groups are analogous to the ones reported here.

EXAMPLE 15

Photostability of Representative Dyes of this Invention

The relative photostability of selected dyes is measured as a decrease of their long-wavelength absorption maximum upon exposure to light. The photostability is compared to Cy5, a long-wavelength standard and a Sulfo-dye with multiple sulfo groups, and the results are shown in FIG. 1.

Figure 2:
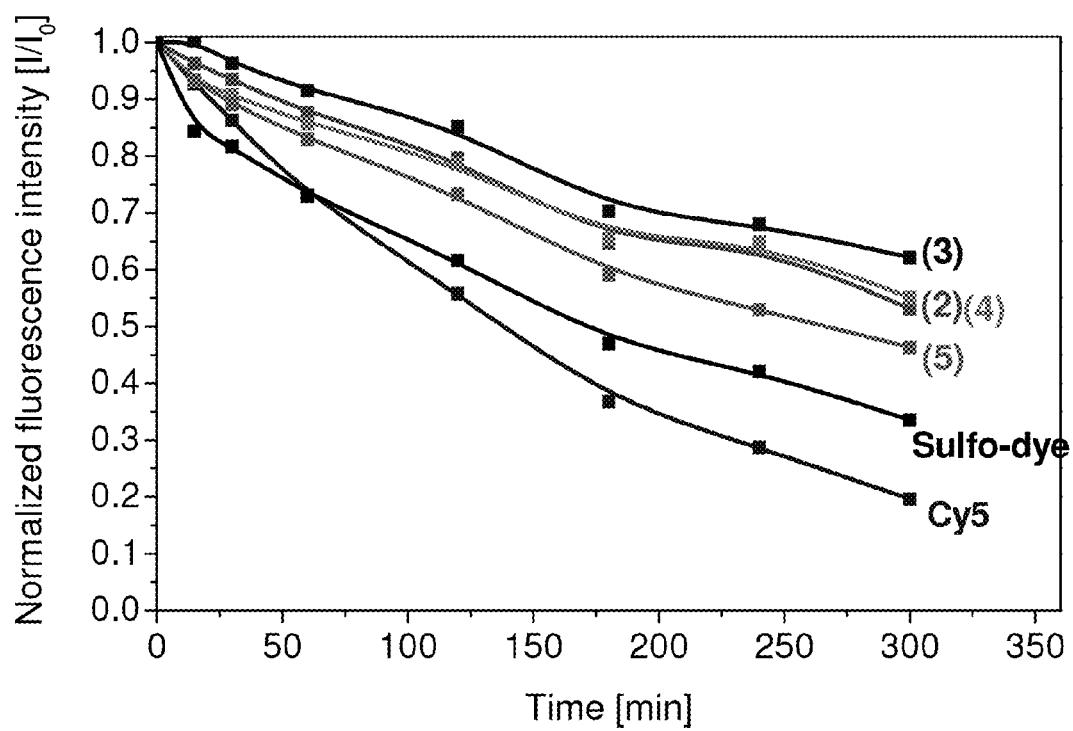
FIG. 2 is a plot showing the relative decrease in fluorescence intensity upon exposure to light for selected dyes, as set forth in Example 15.

The relative photostability of selected dyes is measured as a decrease in fluorescence emission as upon exposure to light. The photostability is compared to Cy5, a long-wavelength standard and a Sulfo-dye with multiple sulfo groups, and the results are shown in FIG. 2.

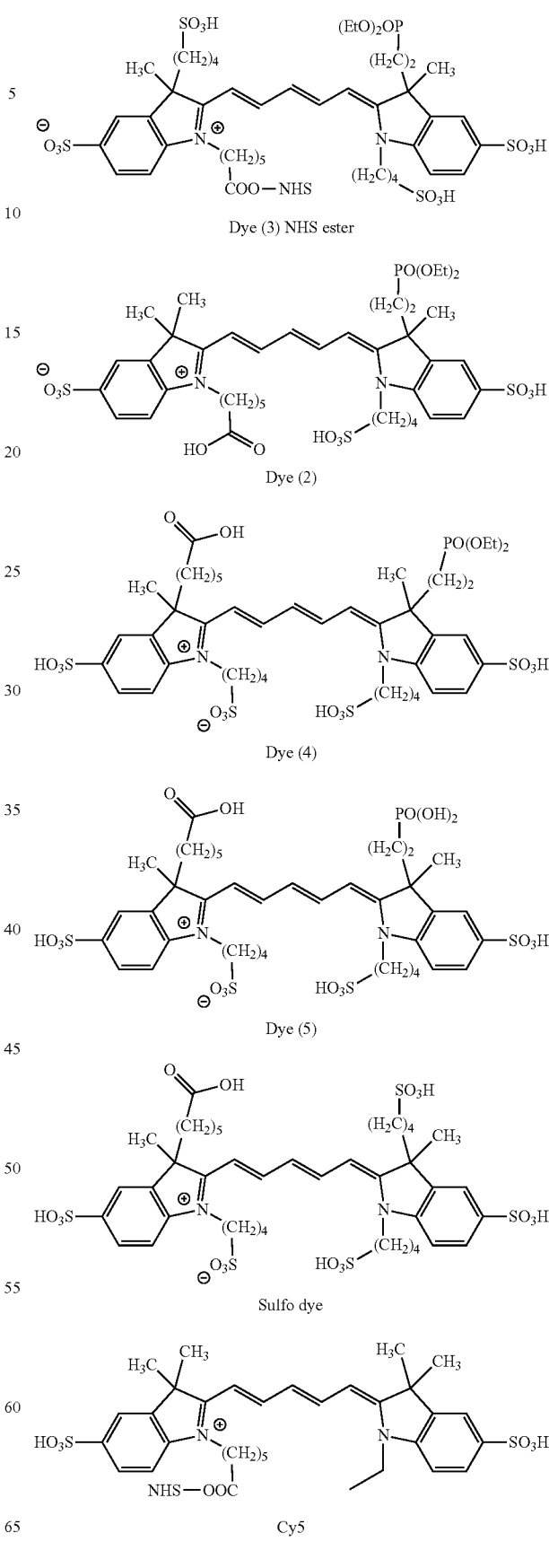

EXAMPLE 16
Selected Embodiments of the Compounds of the Invention
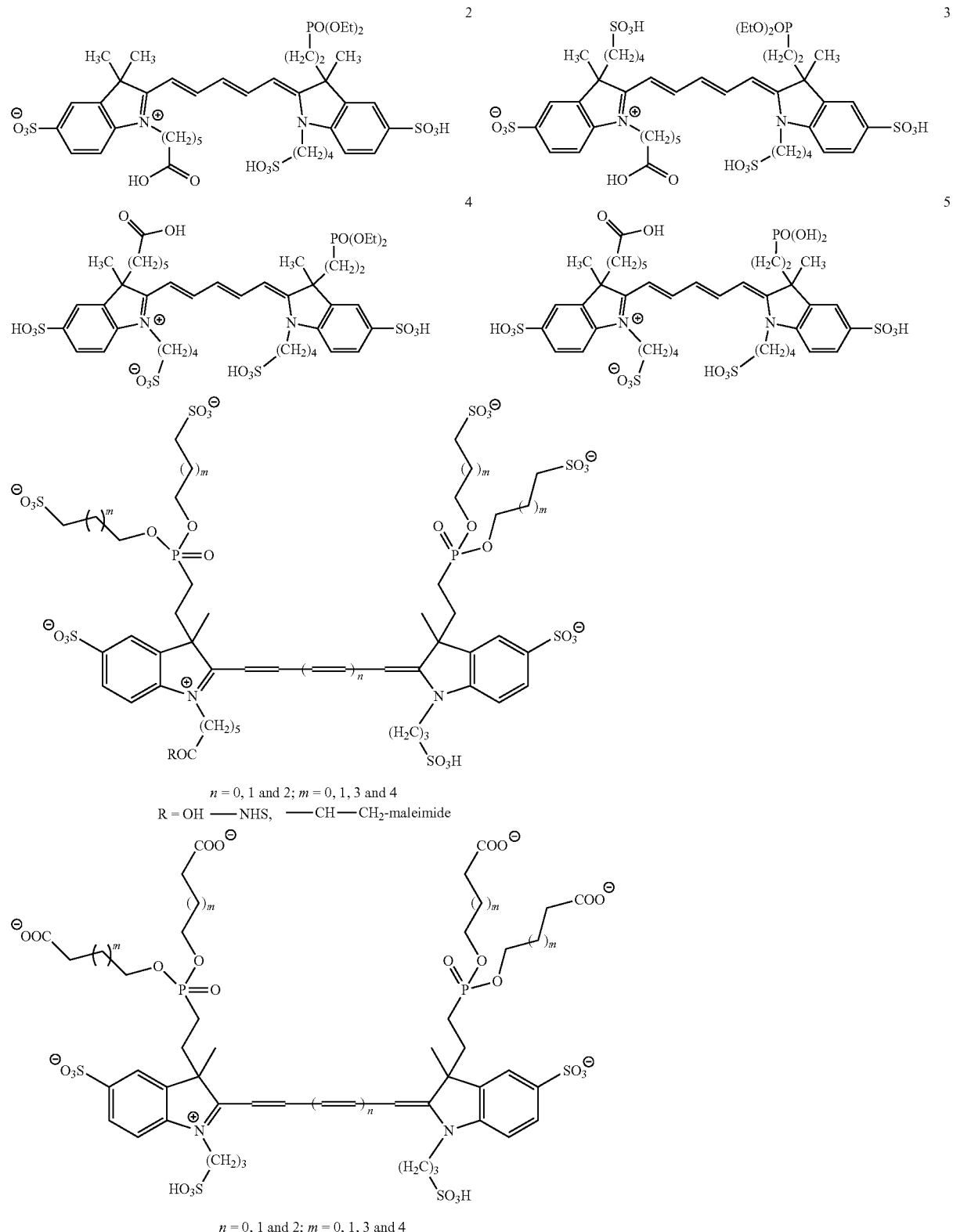

49
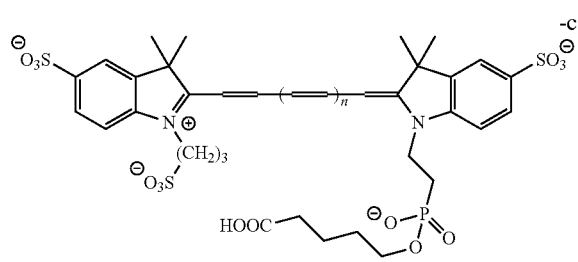
n = 0, 1 and 2
50
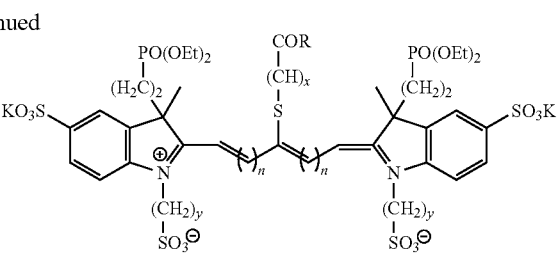
n = 0, 1 and 2; x = 1-4; y = 2-4
R = OH, —NHS, —CH—CH₂-maleimide
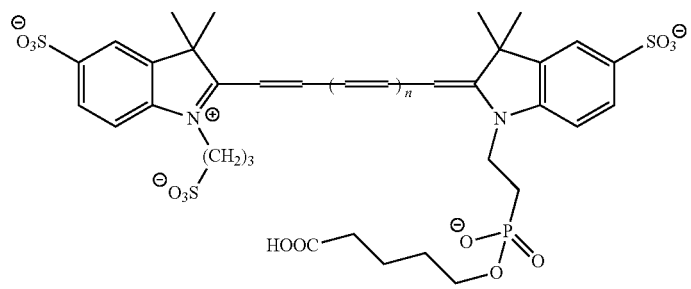
n = 0, 1 and 2
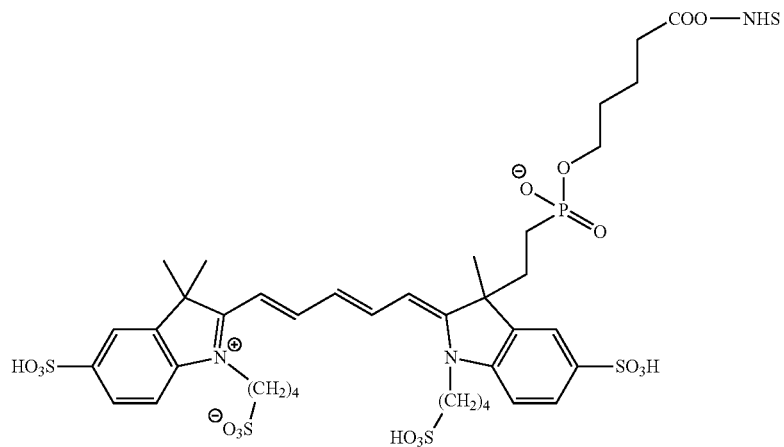
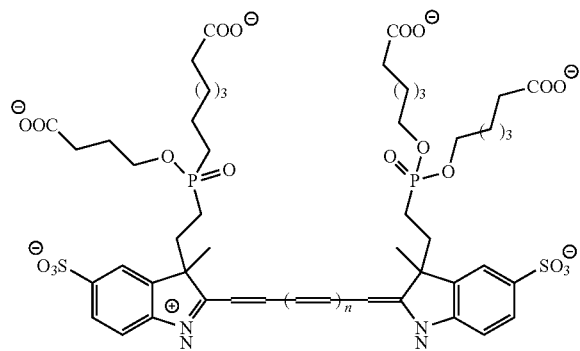
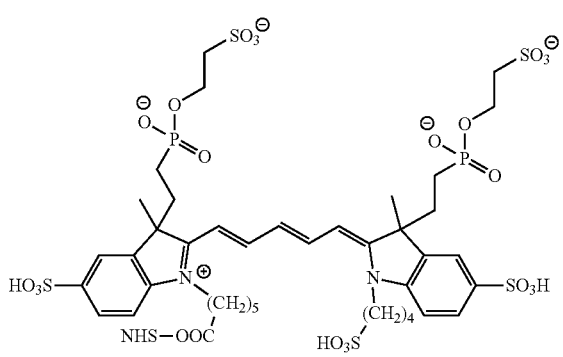

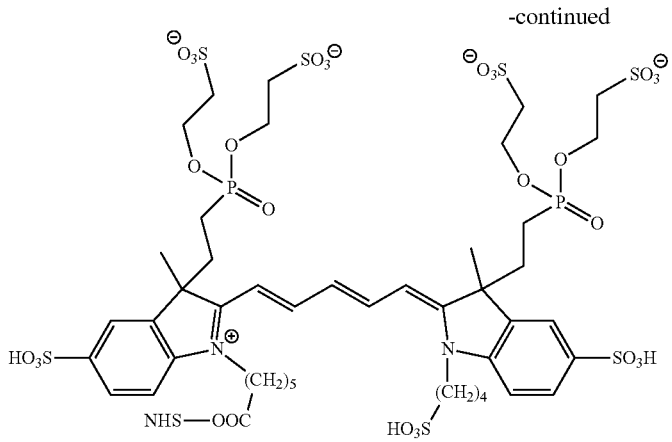

Description of Applications of the Invention

The reporter compounds disclosed above exhibit utility for a variety of useful methods for various assay formats.

The assay may be a competitive assay that includes a recognition moiety, a binding partner, and an analyte. Binding partners and analytes may be selected from the group consisting of biomolecules, drugs, and polymers, among others. In some competitive assay formats, one or more components are labeled with photoluminescent compounds in accordance with the invention. For example, the binding partner may be labeled with such a photoluminescent compound, and the displacement of the compound from an immobilized recognition moiety may be detected by the appearance of fluorescence in a liquid phase of the assay. In other competitive assay formats, an immobilized enzyme may be used to form a complex with the fluorophore-conjugated substrate.

The binding of antagonists to a receptor can be assayed by a competitive binding method in so-called ligand/receptor assays. In such assays, a labeled antagonist competes with an unlabeled ligand for the receptor binding site. One of the binding partners can be, but not necessarily has to be, immobilized. Such assays may also be performed in microplates. Immobilization can be achieved via covalent attachment to the well wall or to the surface of beads.

Other preferred assay formats are immunological assays. There are several such assay formats, including competitive binding assays, in which labeled and unlabeled antigens compete for the binding sites on the surface of an antibody (binding material). Typically, there are incubation times required to provide sufficient time for equilibration. Such assays can be performed in a heterogeneous or homogeneous fashion.

Sandwich assays may use secondary antibodies and excess binding material may be removed from the analyte by a washing step.

Other types of reactions include binding between avidin and biotin, protein A and immunoglobulins, lectins and sugars (e.g., concanavalin A and glucose).

Certain dyes of the invention are charged due to the presence sulfonic groups. These compounds are impermeant to membranes of biological cells. In these cases treatments such as electroporation and shock osmosis can be used to introduce the dye into the cell. Alternatively, such dyes can be physically inserted into the cells by pressure microinjection, scrape loading etc.

The reporter compounds described here also may be used to sequence nucleic acids and peptides. For example, fluorescently-labeled oligonucleotides may be used to trace DNA fragments. Other applications of labeled DNA primers include fluorescence in-situ hybridization methods (FISH) and for single nucleotide polymorphism (SNIPS) applications, among others.

Multicolor labeling experiments may permit different biochemical parameters to be monitored simultaneously. For this purpose, two or more reporter compounds are introduced into the biological system to report on different biochemical functions. The technique can be applied to fluorescence in-situ hybridization (FISH), DNA sequencing, fluorescence microscopy, and flow cytometry. One way to achieve multicolor analysis is to label biomolecules such as nucleotides, proteins or DNA primers with different luminescent reporters having distinct luminescence properties. Luminophores with narrow emission bandwidths are preferred for multicolor labeling, because they have only a small overlap with other dyes and hence increase the number of dyes possible in a multicolor experiment. Importantly, the emission maxima have to be well separated from each other to allow sufficient resolution of the signal. A suitable multicolor triplet of fluorophores would include a Cy3-analog of this invention, TRITC, and a Cy5-analog as described herein, among others.

Phosphoramidites are useful functionalities for the covalent attachment of dyes to oligos in automated oligonucleotide synthesizers. They are easily obtained by reacting the hydroxyalkyl-modified dyes of the invention with 2-cyanoethyl-tetraisopropyl-phosphorodiamidite and 1-H tetrazole in methylene chloride.

The simultaneous use of FISH (fluorescence in-situ hybridization) probes in combination with different fluorophores is useful for the detection of chromosomal translocations, for gene mapping on chromosomes, and for tumor diagnosis, to name only a few applications. One way to achieve simultaneous detection of multiple sequences is to use combinatorial labeling. The second way is to label each nucleic acid probe with a luminophore with distinct spectral properties. Similar conjugates can be synthesized from this invention and can be used in a multicolor multisequence analysis approach.

In another approach the dyes of the invention might be used to directly stain or label a sample so that the sample can be identified and or quantitated. Such dyes might be added/labeled to a target analyte as a tracer. Such tracers could be used e.g. in photodynamic therapy where the labeled compound is irradiated with a light source and thus producing singlet oxygen that helps to destroy tumor cells and diseased tissue samples.

The reporter compounds of the invention can also be used for screening assays for a combinatorial library of compounds. The compounds can be screened for a number of characteristics, including their specificity and avidity for a particular recognition moiety.

Assays for screening a library of compounds are well known. A screening assay is used to determine compounds that bind to a target molecule, and thereby create a signal change which is generated by a labeled ligand bound to the target molecule. Such assays allow screening of compounds that act as agonists or antagonists of a receptor, or that disrupt a protein-protein interaction. It also can be used to detect hybridization pr binding of DNA and/or RNA.

Other screening assays are based on compounds that affect the enzyme activity. For such purposes, quenched enzyme substrates of the invention could be used to trace the interaction with the substrate. In this approach, the cleavage of the fluorescent substrate leads to a change in the spectral properties such as the excitation and emission maxima, intensity and/or lifetime, which allows to distinguish between the free and the bound luminophore.

The reporter compounds disclosed above may also be relevant to single molecule fluorescence microscopy (SMFM) where detection of single probe molecules depends on the availability of a fluorophore with high fluorescence yield, high photostability, and long excitation wavelength.

The dye compounds are also useful for use as biological stains. The dyes are not harmful and non-toxic to cells and other biological components. There may be limitations in some instances to the use of the above compounds as labels. For example, typically only a limited number of dyes may be attached to a biomolecules without altering the fluorescence properties of the dyes (e.g. quantum yields, lifetime, emission characteristics, etc.) and/or the biological activity of the bioconjugate. Typically quantum yields may be reduced at higher degrees of labeling. Encapsulation into beads offers a means to overcome the above limitation for the use of such compounds as fluorescent markers. Fluorescent beads and polymeric materials are becoming increasingly attractive as labels and materials for bioanalytical and sensing applications. Various companies offer particles with defined sizes ranging from nanometers to micrometers. Noncovalent encapsulation in beads may be achieved by swelling the polymer in an organic solvent, such as toluene or chloroform, containing the dye. Covalent encapsulation may be achieved using appropriate reactive functional groups on both the polymer and the dyes.

Compounds claimed here may be also used for covalent and non-covalent stains of proteins and other biomolecules in gel-electrophoresis applications.

In general, hydrophobic versions of the invention may be used for non-covalent encapsulation in polymers, and one or more dyes could be introduced at the same time. Surface-reactive fluorescent particles allow covalent attachment to molecules of biological interest, such as antigens, antibodies, receptors etc. Hydrophobic versions of the invention such as dye having lipophilic substituents such as phospholipids will non-covalently associate with lipids, liposomes, lipoproteins. They are also useful for probing membrane structure and membrane potentials.

Compounds of this invention may also be attached to the surface of metallic nanoparticles such as gold or silver nanoparticles. It has recently been demonstrated that fluorescent molecules may show increased quantum yields near metallic nanostructures e.g. gold or silver nanoparticles (O. Kulakovich et al., Nanoletters 2 (12) 1449-52, 2002). This enhanced fluorescence may be attributable to the presence of a locally enhanced electromagnetic field around metal nanostructures. The changes in the photophysical properties of a fluorophore in the vicinity of the metal surface may be used to develop novel assays and sensors. In one example the nanoparticle may be labeled with one member of a specific binding pair (antibody, protein, receptor etc) and the complementary member (antigen, ligand) may be labeled with a fluorescent molecule in such a way that the interaction of both binding partners leads to an detectable change in one or more fluorescence properties (such as intensity, quantum yield, lifetime, among others). Replacement of the labeled binding partner from the metal surface may lead to a change in fluorescence that can then be used to detect and/or quantify an analyte.

Gold colloids can be synthesized by citrate reduction of a diluted aqueous $HAuCl_4$ solution. These gold nanoparticles are negatively charged due to chemisorption of citrate ions. Surface functionalization may be achieved by reacting the nanoparticles with thiolated linker groups containing amino or carboxy functions. In another approach, thiolated biomolecules are used directly for coupling to these particles.

In a study researchers made the observation that the fluorescence signals of cyanine dyes such as CY5 dye and the ALEXA 647 dyes in microarrays are strongly dependent on the concentration of ozone during posthybridization array washing (T. Fare et al., Anal. Chem. 75(17), 4672-4675, 2003). Controlled exposures of microarrays to ozone confirmed this factor as the root cause, and showed the susceptibility of a class of cyanine dyes (e.g., CY5 dyes, ALEXA 647 dyes) to ozone levels as low as 5 ppb for periods as short as 10 s.

One of the significant findings was the low dose level (ozone concentration multiplied by exposure time) that could induce the onset of the phenomenon, suggesting many labs may be at risk. For example, it is not uncommon that the environmental ozone levels would exceed 60 ppb during peak traffic hours on a sunny summer afternoon. Reporter compounds present on or in arrays that are exposed to these levels for as short as 1 min may begin to show significant degradation in a typical laboratory setting.

There are ways that help to eliminate the occurrence of ozone effects on microarrays, for example equipping laboratories with HVAC systems having filters to significantly reduce ozone levels, or the use of dye-protecting solutions to avoid signal degradation. However, each of these approaches may add additional costs and/or time to perform the assay. These findings suggest the need for dyes and labels in the 600 to 700 nm wavelength range with improved chemical and photochemical stability.

Experimental data on cyanine dyes indicate that introduction of electron-withdrawing groups into the dye backbone may increase the photostability of such dyes.

Analytes

The invention may be used to detect an analyte that interacts with a recognition moiety in a detectable manner. As such, the invention can be attached to a recognition moiety which is known to those of skill in the art. Such recognition moieties allow the detection of specific analytes. Examples are pH-, or potassium sensing molecules, e.g., synthesized by introduction of potassium chelators such as crown-ethers (aza crowns, thia crowns etc). Dyes with N—H substitution in the heterocyclic rings are known to exhibit pH-sensitive absorption and emission (S. Miltsov et al., Tetrahedron Lett. 40: 4067-68, (1999), M. E. Cooper et al., J. Chem. Soc. Chem. Commun. 2000, 2323-2324), Calcium-sensors based on the BAPTA (1,2-Bis(2-aminophenoxy)ethan-N,N,N',N'-tetraaceticacic) chelating moiety are frequently used to trace intracellular ion concentrations. The combination of a compound of the invention and the calcium-binding moiety BAPTA may lead to new long-wavelength absorbing and emitting Ca-sensors which could be used for determination of intra- and extracellular calcium concentrations (Akkaya et al. Tetrahedron Lett. 38:4513-4516 (1997). Additionally, or in the alternative, reporter compounds already having a plurality of carboxyl functional groups may be directly used for sensing and/or quantifying physiologically and environmentally relevant ions.

Fluorescence Methods

The disclosed reporter compounds may be detected using common intensity-based fluorescence methods. The squaraine dyes are known to have lifetimes in the range of hundreds of ps to a few ns (see Example 16). The nanosecond lifetime and long-wavelength absorption and emission of these dyes when bound to proteins may allow them to be measured using relatively inexpensive instrumentation that employs laser diodes for excitation and avalanche photo-diodes for detection. Typical assays based on the measurement of the fluorescence lifetime as a parameter include for example FRET (fluorescence resonance energy transfer) assays. The binding between a fluorescent donor labeled species (typically an antigen) and a fluorescent acceptor labeled species may be accompanied by a change in the intensity and the fluorescence lifetime. The lifetime can be measured using intensity- or phase-modulation-based methods (J. R. Lakowicz, Principles of Fluorescence Spectroscopy ($2^{nd}$ Ed. 1999)).

Cyanine dyes exhibit high intrinsic polarization in the absence of rotational motion, making them useful as tracers in fluorescence polarization (FP) assays. Fluorescence polarization immunoassays (FPI) are widely applied to quantify low molecular weight antigens. The assays are based on polarization measurements of antigens labeled with fluorescent probes. The requirement for polarization probes used in FPIs is that emission from the unbound labeled antigen be depolarized and increase upon binding to the antibody. Low molecular weight species labeled with the compounds of the invention can be used in such binding assays, and the unknown analyte concentration is determined by the change in polarized emission from the fluorescent tracer molecule.

Compositions and Kits

The invention also provides compositions, kits and integrated systems for practicing the various aspects and embodiments of the invention, including producing the novel compounds and practicing of assays. Such kits and systems may include a reporter compound as described above, and may optionally include one or more of solvents, buffers, calibration standards, enzymes, enzyme substrates, and additional reporter compounds having similar or distinctly different optical properties.

Although the invention has been disclosed in preferred forms, the specific embodiments thereof as disclosed and illustrated herein are not to be considered in a limiting sense, because numerous variations are possible. Applicant regards the subject matter of his invention to include all novel and nonobvious combinations and subcombinations of the various elements, features, functions, and/or properties disclosed herein. No single element, feature, function, or property of the disclosed embodiments is essential. The following claims define certain combinations and subcombinations of elements, features, functions, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

We claim:

1. A composition comprising a reporter compound having the formula:

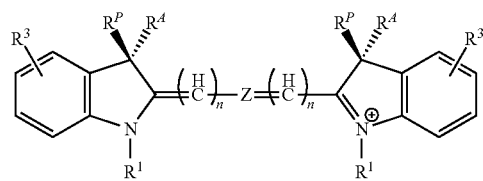

and its salts, or

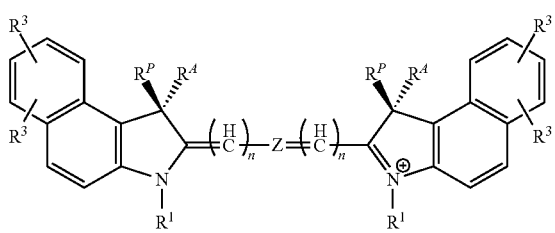

and its salts, or

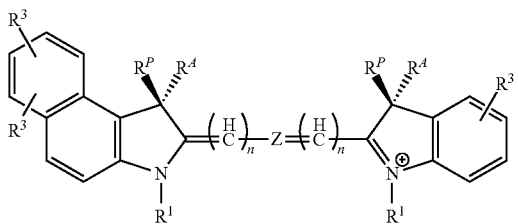

and its salts, where:

n is an integer from 0 to 3;

each $R^1$ independently is —H, a linked reactive group, a linked ionic group, a linked conjugated substance, a linked phosphonate group, a linked substituted alkyl phosphonate group, or an aliphatic group optionally substituted by 1-6 heteroatoms independently selected from the group of N, O, and S;

Z is

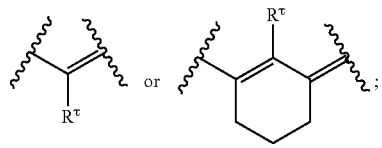

each $R^\tau$ independently is -H, a linked reactive group, a linked ionic group, a linked conjugated substance, or an aliphatic group optionally substituted by 1-6 heteroatoms independently selected from the group of N, O, and S;

each $R^3$ independently is —H, a sulfo group, or an aliphatic group optionally substituted by 1-6 heteroatoms independently selected from the group of N, O, and S;

each $R^4$ independently is —H, or an aliphatic group optionally substituted by 1-6 heteroatoms independently selected from the group of N, O, and S;

each $R^P$ independently is —H, a linked phosphonate group, a linked substituted alkyl phosphonate group, a linked reactive group, a linked ionic group, a linked conjugated substance, or an aliphatic group optionally substituted by 1-6 heteroatoms independently selected from the group of N, O, and S;

wherein at least one $R^P$ is a linked substituted alkyl phosphonate group or a linked phosphonate group except when at least one $R^1$ is a linked substituted alkyl phosphonate group or a linked phosphonate group;

provided that one $R^P$ is a linked reactive group or a linked conjugated substance $S_c$, when the other $R^P$ or at least one $R^1$ is a linked phosphonate group;

provided that at least one of $R^1$ and $R^3$ contains a sulfo group except when at least one $R^P$ substituent is a linked substituted alkyl phosphonate group;

wherein each linked phosphonate group, when present, independently is -L-$PO_3^\ominus$, -L-$PO_3^{2\ominus}$, or -L-$PO(OH)_2$;

wherein each linked substituted alkyl phosphonate, when present, independently is -L-$PO_2(OR^M)^\ominus$, or -L-$PO(OR^M)_2$, where each $R^M$ independently is H, a linked reactive group, a linked ionic group, or a linked conjugated substance, provided that at least one $R^M$ is a linked reactive group, a linked ionic group, or a linked conjugated substance; and wherein L is an aliphatic group optionally substituted by 1-6 heteroatoms independently selected from the group of N, O, and S.

2. The composition of claim 1, wherein at least one $R^P$ is —$(CH_2)_m$ $PO_3(R^N)^\ominus$, or —$(CH_2)_m PO_3(R^N)_2$; wherein m is an integer from 1 to 10; and wherein each $R^N$ independently is H, a linked reactive group, a linked ionic group, or a linked conjugated substance.

3. The composition of claim 1, wherein at least one of $R^1$, $R^\tau$, and $R^P$ comprises a reactive group independently selected from the group consisting of an acylamide, an activated ester of a carboxylic acid, an acyl nitrile, an aldehyde, an alkyl halide, an alkyne, an anhydride, an aniline, an aryl halide, an aziridine, an azide, a boronate, a carboxylic acid, a diazoalkane, a cycloolefin, a haloacetamide, a halotriazine, a hydrazone, an imido ester, an isothiocyanate, an isocyanate, a maleimide, a phosphoramidite, a pyrylium moiety, a reactive platinum complex, a sulfuryl halide, a thiol group, and a photoactivatable group.

4. The composition of claim 1, wherein at least one of $R^1$, $R^\tau$, and $R^P$ comprises an reactive group independently selected from the group consisting of an N-hydroxysuccinimide ester, an isothiocyanate, a sulfonylhalogenide, an azide, an iodoacetamide and a maleimide.

5. The composition of claim 1, wherein at least one of $R^1$, $R^\tau$, and $R^P$ comprises a conjugated substance.

6. The composition of claim 5, wherein at least one of $R^1$, $R^\tau$, and $R^P$ comprises a conjugated substance independently selected from the group consisting of an antibody, a protein, a phycobiliprotein, a polypeptide and a peptide.

7. The composition of claim 5, wherein at least one of $R^1$, $R^\tau$, and $R^P$ comprises a conjugated substance independently selected from the group consisting of a nucleotide, a polynucleotide, a bead, a microplate well surface, a phospholipid, a metallic nanoparticle, an amino acid, a nucleic acid, a protein nucleic acid, a sugar, a polysaccharide, an oligosaccharide, a fluorescent dye, a non-fluorescent dye, and a reporter compound.

8. The composition of claim 1, wherein at least one of $R^1$, $R^3$, $R^\tau$, and $R^P$ comprises an ionic group, wherein the ionic group increases the hydrophilicity of the entire compound.

9. The composition of claim 1, wherein at least one of $R^1$, $R^3$, $R^\tau$, and $R^P$ comprises an ionic group independently selected from the group consisting of —$SO_3^\ominus$, —$OSO_3^\ominus$, —$COO^\ominus$, —$PO_3^{2\ominus}$, —$OPO_3^{2\ominus}$, —$PO_3(R_5)^\ominus$, —$OPO_3(R_5)^\ominus$, and —$N(R^5)_3^\oplus$; wherein each $R^5$ independently is —H, a linked reactive group, a linked conjugated substance, an aromatic group, or an aliphatic group optionally substituted by 1-6 heteroatoms independently selected from the group of N, O, and S.

10. The composition of claim 1, wherein the reporter compound is a first reporter compound, and further comprising a second reporter compound selected from the group consisting of a luminophore and a chromophore.

11. The composition of claim 10, wherein one of the first reporter compound and the second reporter compound is a Förster resonance energy transfer (FRET) donor and the other of the first reporter compound and the second reporter compound is a FRET acceptor.

12. The composition of claim 10, wherein the second reporter compound is a phycobiliprotein.

13. The composition of claim 1, wherein the linked reactive group, the linked ionic group, the linked conjugated substance, the linked phosphonate group, and the linked substituted alkyl phosphonate group, when present, are each linked by an independent linking group, wherein each independent linking group independently is an aliphatic group optionally substituted by 1-6 heteroatoms independently selected from the group of N, O, and S, or a polyether $(CH_213\ CH_2—O)_m$, or $(CH_2)_m—NH—CO—(CH_2)_m$, wherein m is an integer from 1 to 10.

14. The composition of claim 1, wherein the reporter compound has the formula:

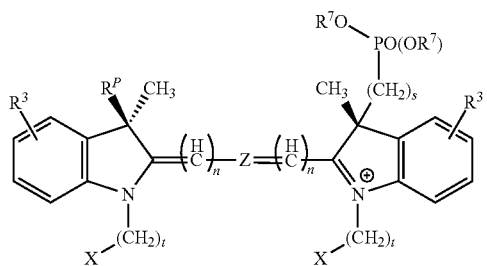

and its salts, or

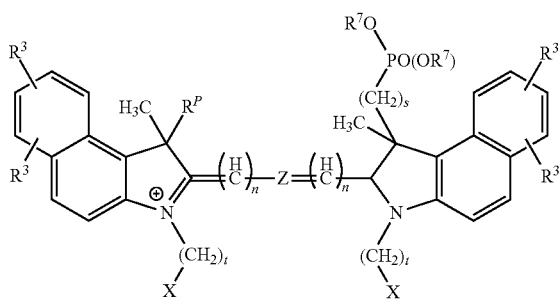

and its salts, or

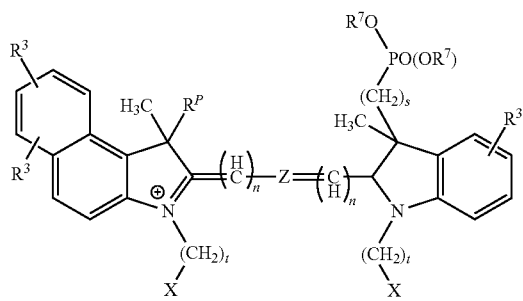

where:

each $R^3$ independently is H, alkyl, or sulfo;

$R^P$ is alkyl, a linked reactive group, or a linked conjugated substance $S_c$;

each $R^7$ independently is H, a linked reactive group, a linked ionic group, or a linked conjugated substance;

each X independently is —H, a linked reactive group, a linked ionic group, a linked conjugated substance $S_c$, a linked phosphonate, a linked substituted alkyl phosphonate group, or $SO_3H$, provided that at least one X is $SO_3H$ when both $R^7$ are H;

$S_c$ is an antibody, an antibody fragment, a protein, a fluorescent protein, a lectin, a nucleotide, an oligonucleotide, a peptide, a polypeptide, a nanoparticle, a protein nucleic acid, a small drug, a phospholipid, a metallic semiconductor, a metallic dielectric nanoparticle, a nanotube, an amino acid, a nucleic acid, a sugar, a polysaccharide, an oligosaccharide, a second fluorescent or non-fluorescent dye, or a tyramide;

each s independently is an integer from 1 to 6;

each t independently is an integer from 0 to 6;

n is an integer from 0 to 3; and provided that $R^P$ is a linked reactive group or a linked conjugated substance $S_c$ when both $R^7$ are H.

15. The composition of claim 1, wherein the reporter compound has the formula:

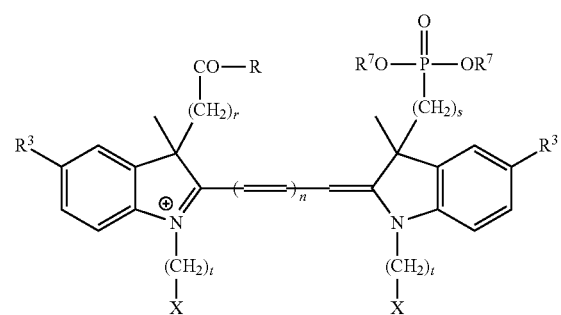

or its diastereomers, where R is independently a reactive group or a linked conjugated substance $S_c$;

$R^7$ is independently H, a linked reactive group, a linked conjugated substance $S_c$, or a linked ionic group;

$R^3$ is independently H, alkyl, or $SO_3H$;

n is 0 to 3;

r is 1 to 10;

s is 1 to 10;

t is independently 1 to 4; and

X is independently H or $SO_3H$, provided that at least one X is $SO_3H$ when both $R_7$ are H.

16. The composition of claim 1, wherein the reporter compound has the formula:

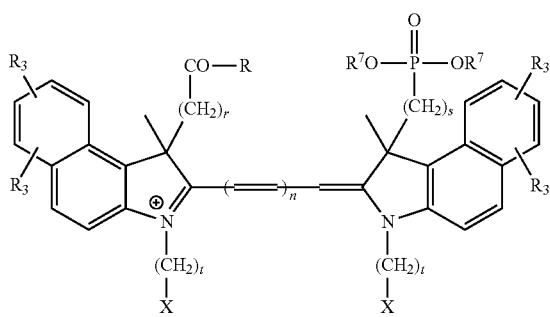

or its diastereomers, where R is independently a reactive group or a linked conjugated substance $S_c$;

$R^7$ is independently H, a linked reactive group, a linked conjugated substance $S_c$, or a linked ionic group;

$R^3$ is independently H, alkyl, or $SO_3H$;

n is 0 to 3;

r is 1 to 10;

s is 1 to 10;

t is independently 1 to 4; and

X is independently H or $SO_3H$, provided that at least one X is $SO_3H$ when both $R^7$ are H.

17. The composition of claim 1, wherein the reporter compound has the formula:

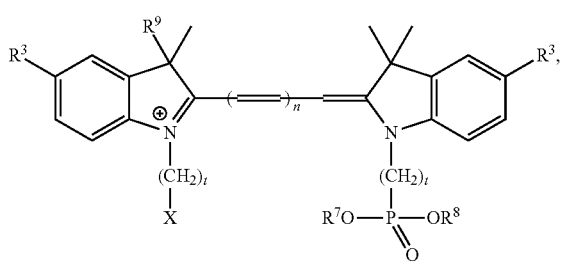

$R^3$ is independently H, alkyl, or $SO_3H$;

$R^7$ is independently H, a linked reactive group, a linked conjugated substance $S_c$, or a linked ionic group;

$R^8$ is independently H, a linked reactive group, a linked conjugated substance $S_c$, or a linked ionic group;

where $R^9$ is independently H, alkyl, a linked reactive group, or a linked conjugated substance $S_c$, provided that $R^9$ is a linked reactive group or a linked conjugated substance $S_c$ when $R^7$ and $R^8$ are H;

n is 0 to 3;

t is independently 1 to 10; and

X is independently H, $SO_3H$, a linked conjugated substance Sc, a reactive group, or a linked substituted alkyl phosphonate group, provided that at least one of X and $R_3$ is $SO_3H$ when $R^7$ and $R^8$ are H.

18. The composition of claim 1, wherein the reporter compound has the formula:

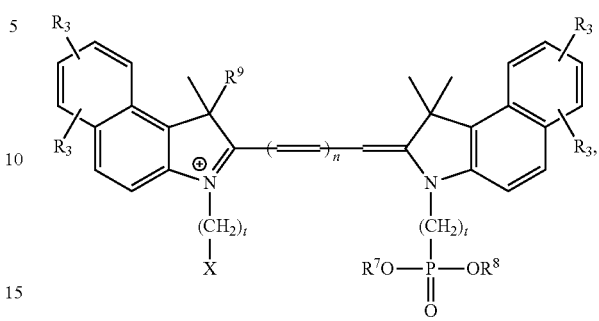

$R^3$ is independently H, alkyl or $SO_3H$;

$R^7$ is independently H, a linked reactive group, a linked conjugated substance $S_c$, or a linked ionic group;

$R^8$ is independently H, a linked reactive group, a linked conjugated substance $S_c$, or a linked ionic group;

where $R^9$ is H, alkyl, a linked reactive group, or a linked conjugated substance $S_c$, provided that $R^9$ is a linked reactive group or a linked conjugated substance $S_c$ when $R^7$ and $R^8$ are H;

n is 0 to 3;

t is independently 1 to 10; and

X is independently H, $SO_3H$, a linked conjugated substance Sc, a reactive group, or a linked substituted alkyl phosphonate group, provided that one of X and $R_3$ is $SO_3H$ when $R^7$ and $R^8$ are H.

19. The composition of claim 1, wherein the reporter compound has the formula:

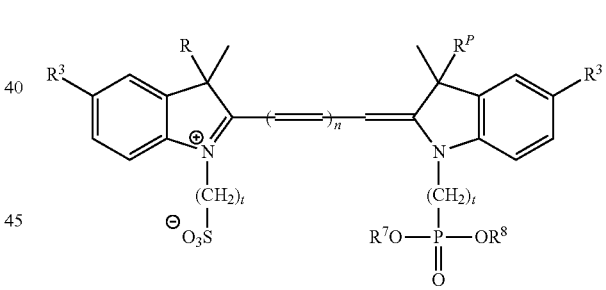

or

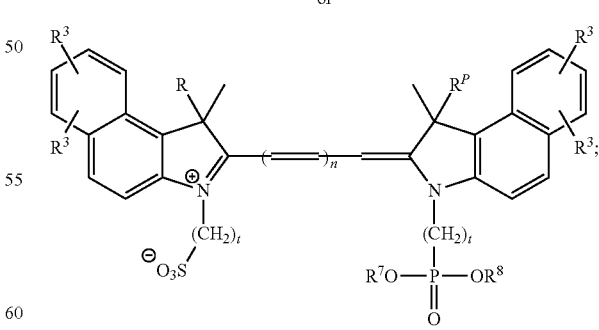

$R^3$ is independently H, alkyl, or $SO_3H$;

$R^7$ is independently H, a linked reactive group, a linked conjugated substance $S_c$, or a linked ionic group;

$R^8$ is independently H, a linked reactive group, a linked conjugated substance $S_c$, or a linked ionic group;

n is 0 to 3;

t is independently 1 to 10; and $R^P$ is an alkyl group, a linked reactive group, a linked ionic group, or a linked conjugated substance $S_c$; and R is a linked reactive group or a linked conjugated substance $S_c$.

\* \* \* \* \*

UNITED STATES PATENT AND TRADEMARK OFFICE
CERTIFICATE OF CORRECTION

PATENT NO. : 9,110,069 B2  Page 1 of 1
APPLICATION NO. : 14/047878
DATED : August 18, 2015
INVENTOR(S) : Ewald A. Terpetschnig et al.

It is certified that error appears in the above-identified patent and that said Letters Patent is hereby corrected as shown below:

In the Claims:

Column 57, line 62, after "independently is" please delete "-L-PO$_3^{\square}$, -L-PO$_3^{2\square}$" and insert -- -L-PO$_3^{2\square}$, -L-PO$_3$H$^{\square}$ --.

Column 59, line 15, after "the group of N, O, and S, or a polyether" please delete "(CH$_2$13CH$_2$—O)$_m$," and insert -- (CH$_2$-CH$_2$-O)$_m$, --.

Signed and Sealed this
First Day of March, 2016

Michelle K. Lee
*Director of the United States Patent and Trademark Office*

UNITED STATES PATENT AND TRADEMARK OFFICE
CERTIFICATE OF CORRECTION

PATENT NO. : 9,110,069 B2  
APPLICATION NO. : 14/047878  
DATED : August 18, 2015  
INVENTOR(S) : Ewald A. Terpetschnig et al.

It is certified that error appears in the above-identified patent and that said Letters Patent is hereby corrected as shown below:

In the Claims:

Column 57, line 62, after "independently is" please delete "-L-$PO_3^{\ominus}$, -L-$PO_3^{2\ominus}$" and insert -- -L-$PO_3^{2\ominus}$, -L-$PO_3H^{\ominus}$--.

Column 59, line 15, after "the group of N, O, and S, or a polyether" please delete "($CH_2$13$CH_2$—O)$_m$," and insert --($CH_2$-$CH_2$-O)$_m$,--.

This certificate supersedes the Certificate of Correction issued March 1, 2016.

Signed and Sealed this  
Twenty-first Day of June, 2016

Michelle K. Lee  
*Director of the United States Patent and Trademark Office*